US010048195B2

(12) United States Patent
Hedges et al.

(10) Patent No.: US 10,048,195 B2
(45) Date of Patent: Aug. 14, 2018

(54) OXYGEN ANALYSIS SYSTEM AND METHOD FOR MEASURING, MONITORING AND RECORDING OXYGEN CONCENTRATION IN AIRCRAFT FUEL TANKS

(71) Applicant: The Boeing Company, Chicago, IL (US)

(72) Inventors: Daniel E. Hedges, Kirkland, WA (US); Mark J. Holland, Port Orchard, WA (US); Scott S. Rhodes, Seattle, WA (US); Jennifer D. Klemisch, Seattle, WA (US); Jessica C. Pavia, Everett, WA (US); Thomas Michael Henry, Burien, WA (US); Clay J. Anderson, Seattle, WA (US); Bruce W. McCaul, Palo Alto, CA (US); Thomas Mac Winsemius, Soquel, CA (US); Eric K. Thorson, Port Townsend, WA (US)

(73) Assignee: The Boeing Company, Chicago, IL (US)

( * ) Notice: Subject to any disclaimer, the term of this patent is extended or adjusted under 35 U.S.C. 154(b) by 641 days.

(21) Appl. No.: 14/170,558

(22) Filed: Jan. 31, 2014

(65) Prior Publication Data

US 2015/0219554 A1 Aug. 6, 2015

(51) Int. Cl.
*B64D 37/32* (2006.01)
*G01N 21/39* (2006.01)

(52) U.S. Cl.
CPC ............. *G01N 21/39* (2013.01); *B64D 37/32* (2013.01); *G01N 2021/399* (2013.01); *G01N 2201/0214* (2013.01); *G01N 2201/0407* (2013.01)

(58) Field of Classification Search
CPC ................................ G01N 21/39; B64D 37/32
See application file for complete search history.

(56) References Cited

U.S. PATENT DOCUMENTS 2,962,360 A * 11/1960 Bennet ..................... G01N 7/04
361/166
5,047,639 A 9/1991 Wong
(Continued)

FOREIGN PATENT DOCUMENTS

EP 0729565 B1 3/2003

OTHER PUBLICATIONS

Reynolds, Thomas L., et al., "Onboard Inert Gas Generation System/Onboard Oxygen Gas Generation System (OBIGGS/OBOGS) Study, Part II: Gas Separation Technology—State of the Art", NASA/CR-2001-210950, Aug. 2001, 72 pages.
(Continued)

*Primary Examiner* — Lisa Caputo
*Assistant Examiner* — Alex Devito

(57) ABSTRACT

An oxygen analysis system (OAS) for measuring, monitoring and recording oxygen concentration in aircraft fuel tanks. The OAS has a rack support structure installed in an aircraft cabin with a plurality of oxygen analyzer devices mounted in the rack support structure. Each oxygen analyzer device has an oxygen sensor to measure oxygen concentration in gas samples continuously drawn from sample locations in aircraft fuel tanks and at an aircraft NGS ASM exit. The OAS further has a plurality of valves, a supply of calibration gases, a supply of purge and operating gases, and a power distribution assembly, all coupled to the rack support structure. The OAS further has a transport tubing assembly, a plurality of fuel tank gas sampling ports, an NGS ASM exit gas sampling port, a drain manifold assem-
(Continued)

bly, and a data acquisition and recording system having a user interface software to monitor and control the OAS.

21 Claims, 12 Drawing Sheets

(56) References Cited

U.S. PATENT DOCUMENTS

| | | | |
|---|---|---|---|
| 5,448,071 A | 9/1995 | McCaul et al. |
| 5,491,341 A | 2/1996 | McCaul et al. |
| 5,500,768 A | 3/1996 | Doggett et al. |
| 5,615,052 A | 3/1997 | Doggett |
| 5,625,189 A | 4/1997 | McCaul et al. |
| 6,150,661 A | 11/2000 | McCaul et al. |
| 6,189,516 B1 | 2/2001 | Hei Ma |
| 6,585,192 B2 | 7/2003 | Beers |
| 6,634,598 B2 | 10/2003 | Susko |
| 7,013,905 B2 | 3/2006 | Jones et al. |
| 7,352,464 B2 | 4/2008 | Chen et al. |
| 7,481,237 B2 | 1/2009 | Jones et al. |
| 7,574,894 B2 | 8/2009 | Austerlitz et al. |
| 7,625,434 B2 | 12/2009 | Tom et al. |
| 7,896,292 B2 | 3/2011 | Limaye et al. |
| 8,499,567 B2 | 8/2013 | Hagh et al. |
| 2004/0094201 A1 | 5/2004 | Verma et al. |
| 2007/0062371 A1* | 3/2007 | Eilers .............. A62B 7/14 95/138 |
| 2008/0128048 A1 | 6/2008 | Johnson et al. |
| 2009/0166358 A1 | 7/2009 | Bose |

OTHER PUBLICATIONS

Chen, Shin-Juh, et al., "Detection of Explosive Mixtures in the Ullage of Aircraft Fuel Tanks", American Institute of Aeronautics and Astronautics, AIAA-2004-0548, 2004, 10 pages.
Cavage, William, "Measuring Oxygen Concentration in a Fuel Tank Ullage", Federal Aviation Administration, ISFPWG Meeting, Atlantic City, NJ, Nov. 17-18, 2009, 14 pages.
McCaul, Bruce, et al., "OBIGGS Flight Test Validation", Oxigraf SAE AE-5D Committee, Sep. 20, 2011, 24 pages.
OXIGRAF 2012/2013 Price List, Model O2N2 Oxygen Analyzer: Aircraft OBIGGS Validation System, Effective Sep. 1, 2012, 2 pages.

* cited by examiner

OXYGEN ANALYSIS SYSTEM AND METHOD FOR MEASURING, MONITORING AND RECORDING OXYGEN CONCENTRATION IN AIRCRAFT FUEL TANKS

BACKGROUND

1) Field of the Disclosure

The disclosure relates generally to systems and methods for measuring oxygen concentration in fuel tanks, and more specifically, to oxygen analysis systems and methods for measuring, monitoring and recording oxygen concentration in aircraft fuel tanks.

2) Description of Related Art

Nitrogen generation systems ("NGS") may be utilized to reduce the combustibility of aircraft fuel tanks. An NGS produces nitrogen, which is fed into the fuel tanks, and oxygen enriched air as a byproduct. Prior NGS certification testing of an NGS was initially performed with a measurement system supplied by the Federal Aviation Administration (FAA) Technical Center using a system known as "OBOAS" (On-Board Oxygen Analysis System). OBOAS was based on an electrochemical sensor technology. OBOAS worked but required unacceptably high maintenance and operator intervention to ensure adequate data quality. Moreover, OBOAS was not adequately efficient to support the rapid pace of a major test program.

Other known systems and methods were also used for NGS certification testing. One such known system used a single-channel, off-the-shelf oxygen sensor analyzer on select programs where only a single measurement was required at the NGS air separation module (ASM) exit.

However, in later generation aircraft, the NGS applies to the main fuel tanks as well as the center fuel tank, and requires measurements at 22 locations, including 7 measurements in the left main fuel tank, 8 measurements in the center fuel tank, and 6 measurements in the right main fuel tank, plus one measurement at the NGS ASM exit. One known system allowed for 8 measurements. However, additional manual valves needed to be added to permit measurements at the measurement locations. This involved having to manually track valve positions to understand which location was being measured. Moreover, such known system was a manually operated and manually switched system, which was unduly complex and expensive.

Moreover, such prior known systems and methods may require an increased level of monitoring and a high degree of temperature stability, which would not be suitable for such later generation aircraft. Thus, such prior known systems and methods would not be adequate for NGS certification for such later generation aircraft requiring measurements at 22 locations.

Accordingly, what is needed is an improved oxygen analysis system and method for measuring, monitoring and recording oxygen concentration in aircraft fuel tanks that provide advantages over known systems and methods.

SUMMARY

This need for an improved oxygen analysis system and method for measuring, monitoring and recording oxygen concentration in aircraft fuel tanks, is satisfied. As discussed in the below detailed description, embodiments of the oxygen analysis system and method for measuring, monitoring and recording oxygen concentration in aircraft fuel tanks, may provide significant advantages over known systems and methods.

In one embodiment of the disclosure, there is provided an oxygen analysis system (OAS) for measuring, monitoring and recording oxygen concentration in aircraft fuel tanks. The oxygen analysis system comprises a rack support structure installed in an aircraft cabin. The oxygen analysis system further comprises a plurality of oxygen analyzer devices mounted in the rack support structure. Each oxygen analyzer device comprises an oxygen sensor to measure oxygen concentration in gas samples continuously drawn from sample locations in aircraft fuel tanks and at an aircraft nitrogen generation system (NGS) air separation module (ASM) exit.

The oxygen analysis system further comprises a plurality of valves, a supply of calibration gases, a supply of purge and operating gases, and a power distribution assembly, all coupled to the rack support structure. The oxygen analysis system further comprises a transport tubing assembly coupled between the rack support structure and the aircraft fuel tanks and the NGS ASM exit. The transport tubing assembly is configured to transport the gas samples to and from the plurality of oxygen analyzer devices in the rack support structure.

The oxygen analysis system further comprises a plurality of fuel tank gas sampling ports located in the aircraft fuel tanks and an NGS ASM exit gas sampling port located at the NGS ASM exit. The oxygen analysis system further comprises a drain manifold assembly coupled along the transport tubing assembly between the rack support structure and the plurality of fuel tank gas sampling ports and configured to capture and drain liquids that enter into the transport tubing assembly.

The oxygen analysis system further comprises a data acquisition and recording system coupled to the plurality of oxygen analyzer devices, for collecting and processing oxygen concentration data measured by the oxygen sensor of each oxygen analyzer device. The data acquisition and recording system comprises a user interface software to monitor and control the oxygen analysis system.

The oxygen analysis system further comprises a sensor monitoring system to monitor the oxygen sensor of each oxygen analyzer device at a sample rate equal to or greater than about one (1) sample per thirty (30) seconds per sample flow channel. The oxygen analysis system further comprises an automated calibration system using one or more calibration gas concentration values obtained from the supply of calibration gases to calibrate the oxygen analysis system in real time. The calibration gases preferably comprise an oxygen gas having a 5% oxygen concentration and an oxygen gas having a 21% oxygen calibration. The oxygen analysis system may further comprise a verification gas comprising an oxygen gas having a 12% oxygen concentration.

The supply of purge and operating gases preferably comprises a purge gas comprising an oxygen gas having a 3% oxygen concentration to control the plurality of valves and to provide a purge capability in real time to clear blocked sample flow channels of the transport tubing assembly. The oxygen analysis system may further comprise an inerting gas comprising an oxygen gas having a 3% oxygen concentration to maintain an enclosure of each oxygen analyzer device at a 3% oxygen concentration throughout an aircraft flight.

The oxygen sensor is preferably a tunable laser diode oxygen sensor. The plurality of fuel tank gas sampling ports preferably comprise up to twenty-one (21) sample locations in the aircraft fuel tanks. However, more or less than twenty-one (21) sample locations may also be used. The gas samples drawn from sample locations within the aircraft fuel tanks are preferably drawn from an ullage of each aircraft fuel tank.

In another embodiment of the disclosure, there is provided an aircraft having at least one wing, each wing having one or more aircraft fuel tanks, and a fuselage defining an interior aircraft cabin. The aircraft further comprises an oxygen analysis system (OAS).

The oxygen analysis system comprises a rack support structure installed in the aircraft cabin. The oxygen analysis system further comprises a plurality of oxygen analyzer devices mounted in the rack support structure. Each oxygen analyzer device comprises a tunable laser diode oxygen sensor to measure oxygen concentration in gas samples continuously drawn from sample locations in aircraft fuel tanks and at an aircraft nitrogen generation system (NGS) air separation module (ASM) exit.

The oxygen analysis system further comprises a plurality of valves, a supply of calibration gases, a supply of purge and operating gases, and a power distribution assembly, all coupled to the rack support structure. The oxygen analysis system further comprises a transport tubing assembly coupled between the rack support structure and the aircraft fuel tanks and the NGS ASM exit. The transport tubing assembly is configured to transport the gas samples to and from the plurality of oxygen analyzer devices in the rack support structure.

The oxygen analysis system further comprises a plurality of fuel tank gas sampling ports located in the aircraft fuel tanks and an NGS ASM exit gas sampling port located at the NGS ASM exit. The oxygen analysis system further comprises a drain manifold assembly coupled along the transport tubing assembly between the rack support structure and the plurality of fuel tank gas sampling ports and configured to capture and drain liquids that enter into the transport tubing assembly.

The oxygen analysis system further comprises a data acquisition and recording system coupled to the plurality of oxygen analyzer devices, for collecting and processing oxygen concentration data measured by the a tunable laser diode oxygen sensor of each oxygen analyzer device. The data acquisition and recording system comprises a user interface software to monitor and control the oxygen analysis system. The oxygen analysis system measures, monitors and records oxygen concentration in the aircraft fuel tanks in real time.

The oxygen analysis system of the aircraft may further comprise a sensor monitoring system to monitor the oxygen sensor of each oxygen analyzer device at a sample rate equal to or greater than about one (1) sample per thirty (30) seconds per sample flow channel. The oxygen analysis system of the aircraft may further comprise an automated calibration system using one or more calibration gas concentration values obtained from the supply of calibration gases to calibrate the oxygen analysis system in real time. The oxygen analysis system of the aircraft may further comprise an inerting gas and a purge gas both comprising an oxygen gas having a 3% oxygen concentration.

In another embodiment of the disclosure, there is provided an oxygen analysis method for measuring, monitoring and recording oxygen concentration in aircraft fuel tanks. The method comprises the step of installing an oxygen analysis system (OAS) in an aircraft.

The method further comprises the step of continuously drawing fuel tank gas samples from aircraft fuel tanks. The method further comprises the step of introducing a fuel tank gas sample of interest to a tunable laser diode oxygen sensor of the OAS. The method further comprises the step of measuring with the tunable laser diode oxygen sensor an oxygen concentration of the fuel tank gas sample of interest.

The method further comprises the step of drawing an NGS ASM exit gas sample from an NGS ASM exit. The method further comprises the step of introducing an NGS ASM exit gas sample of interest to the tunable laser diode oxygen sensor. The method further comprises the step of measuring with the tunable laser diode oxygen sensor an oxygen concentration of the NGS ASM exit sample of interest.

The method further comprises the step of outputting to a data acquisition and recording system output results of oxygen concentration data measured by the tunable laser diode oxygen sensor. The method further comprises the step of monitoring and recording oxygen concentration in the aircraft fuel tanks in real time. The method further comprises the step of returning the fuel tank gas sample back to the aircraft fuel tank it came from and venting the NGS ASM exit gas sample out of the aircraft.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein.

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and will fully convey the scope of the disclosure to those skilled in the art.

Figure 1:
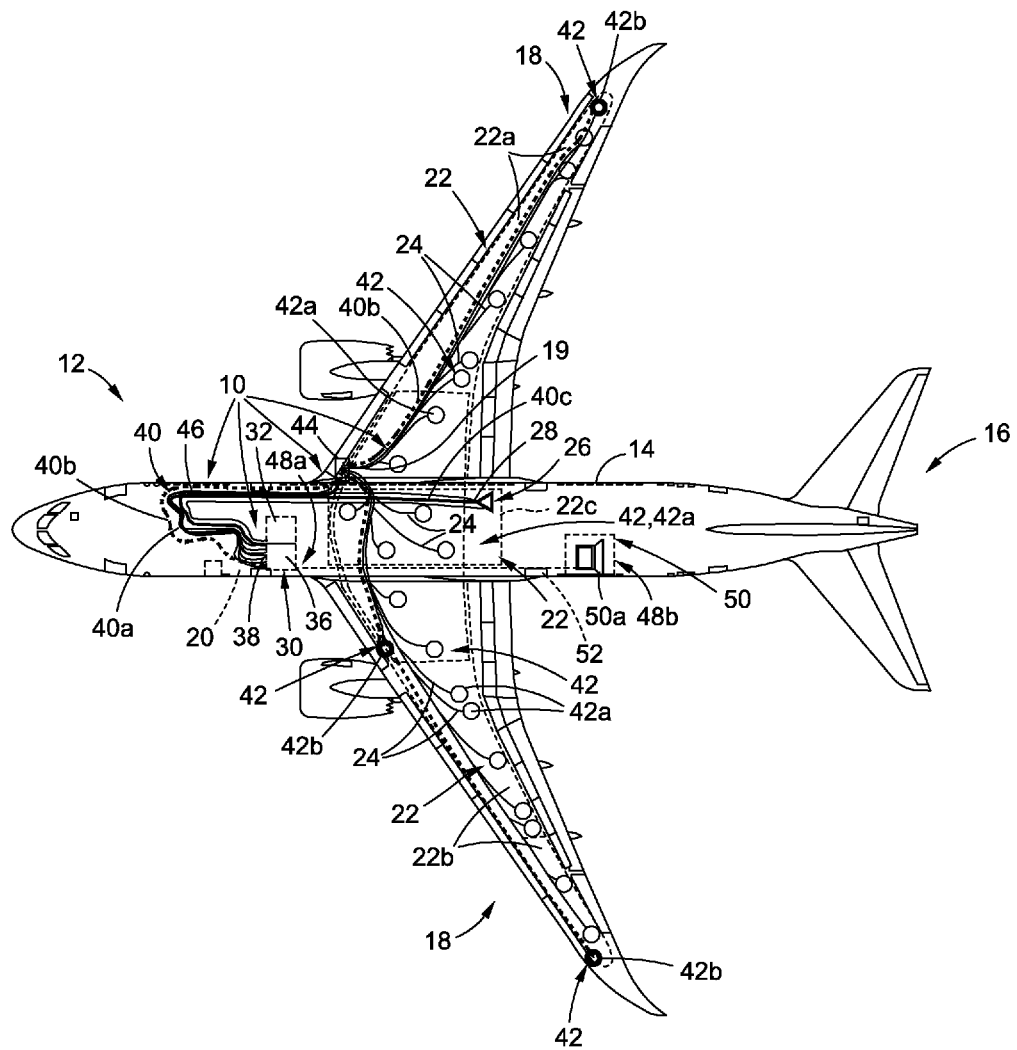
FIG. 1 is an illustration of a plan view of an aircraft that may incorporate an embodiment of an oxygen analysis system (OAS) of the disclosure.

Now referring to the Figures, FIG. 1 is an illustration of a plan view of an aircraft 12 that may incorporate an embodiment of an oxygen analysis system (OAS) 10 of the disclosure. The OAS 10 (see FIGS. 1-3), discussed in detail below, is designed to measure, monitor and record oxygen concentrations 68 (see FIG. 2) in aircraft fuel tanks 22 (see FIGS. 1-3) and at a nitrogen generation system (NGS) air separation module (ASM) exit 26 (see FIG. 1). Preferably, the OAS 10 (see FIGS. 1-3) is a flight test data acquisition and monitoring system 50a (see FIG. 3) designed for real-time measurement 96 (see FIG. 2) and monitoring of oxygen concentration 66 (see FIG. 2).

Further, an oxygen analysis method 200 (see FIG. 7) for measuring, monitoring and recording oxygen concentrations 68 (see FIG. 2) in aircraft fuel tanks 22 (see FIGS. 1-3) and at the NGS ASM exit 26 (see FIG. 1) is disclosed.

As shown in FIG. 1, the aircraft 12 has a fuselage 14, tail 16, one or more wings 18. The fuselage 14 defines an interior aircraft cabin 20 (see FIG. 1) preferably for passengers and an interior cargo bay 19 (see FIG. 1) preferably for cargo. As shown in FIG. 1, aircraft 12 further comprises aircraft fuel tanks 22 in the wings 18. FIG. 1 shows right aircraft fuel tanks 22a, left aircraft fuel tanks 22b, and a center aircraft fuel tank 22c. The oxygen analysis system (OAS) 10 comprises a plurality of fuel tank gas sampling ports 24 (see FIG. 1) in each of the aircraft fuel tanks 22 (see FIG. 1). Preferably, the oxygen analysis system (OAS) 10 has twenty-one (21) fuel tank gas sampling ports 24. More preferably, the oxygen analysis system (OAS) 10 has six (6) fuel tank gas sampling ports 24 in the right aircraft fuel tanks 22a, has seven (7) fuel tank gas sampling ports 24 in the left aircraft fuel tanks 22b, and has eight (8) fuel tank gas sampling ports 24 in the center aircraft fuel tank 22c. However, more or less than twenty-one (21) fuel tank gas sampling ports 24 may also be used.

As shown in FIG. 1, the aircraft 12 further comprises an aircraft nitrogen generation system (NGS) air separation module (ASM) exit 26. The oxygen analysis system (OAS) 10 (see FIG. 1) further comprises an aircraft nitrogen generation system (NGS) air separation module (ASM) exit gas sampling port 28 (see FIG. 1).

As shown in FIG. 1, the oxygen analysis system (OAS) 10 comprises a rack support structure 30 installed in the aircraft cabin 20. The rack support structure 30 (see FIG. 1) comprises an oxygen analyzer device portion 32 (see FIG. 1) and a plumbing portion 36 (see FIG. 1). A plurality of attachments 38 attaching a transport tubing assembly 40 to the rack support structure 30 are shown in FIG. 1. The transport tubing assembly 40 (see FIG. 1) comprises fuel tank sample transport tubing 40a extending between the aircraft fuel tanks 22 and the rack support structure 30 (see FIG. 1). Gas samples 70 (see FIG. 2)), such as in the form of fuel tank gas samples 70a (see FIG. 2), are preferably taken from the plurality of fuel tank gas sampling ports 24 (see FIG. 1) in each of the aircraft fuel tanks 22 (see FIG. 1) and transported via the fuel tank sample transport tubing 40a to the rack support structure 30 (see FIG. 1). In particular, the fuel tank sample transport tubing 40a extends to oxygen analyzer devices 34 mounted in the oxygen analyzer device portion 32 (see FIG. 1) of the rack support structure 30. Once the gas samples 70 (see FIG. 1), such as in the form of fuel tank gas samples 70a (see FIG. 2), are analyzed with the oxygen analyzer devices 34, they are returned to the aircraft fuel tanks 22 via fuel tank return transport tubing 40b extending between the rack support structure 30 (see FIG. 1) and the aircraft fuel tanks 22.

A gas sample 70 (see FIG. 2), such as in the form of NGS ASM exit gas sample 70b (see FIG. 2), is also preferably drawn from the NGS ASM exit gas sampling port 28 (see FIG. 1) and transported via NGS ASM exit sample transport tubing 40c which extends between the NGS ASM exit 26 and rack support structure 30 (see FIG. 1). In particular, to the NGS ASM exit sample transport tubing 40c extends to the oxygen analyzer devices 34 mounted in the oxygen analyzer device portion 32 (see FIG. 1) of the rack support structure 30. Once the gas sample 70 (see FIG. 2), such as in the form of NGS ASM exit gas sample 70b (see FIG. 2), is analyzed with the oxygen analyzer devices 34, it is vented outside the aircraft 12 (see FIG. 1).

As shown in FIG. 1, the oxygen analysis system (OAS) 10 further comprises a plurality of float valves 42, such as in the form of fuel tank sample float valves 42a and fuel tank return float valves 42b. The float valves 42 prevent ingestion of liquid fuel 78 (see FIG. 3) at the sample locations 72 (see FIG. 2).

Figure 6:
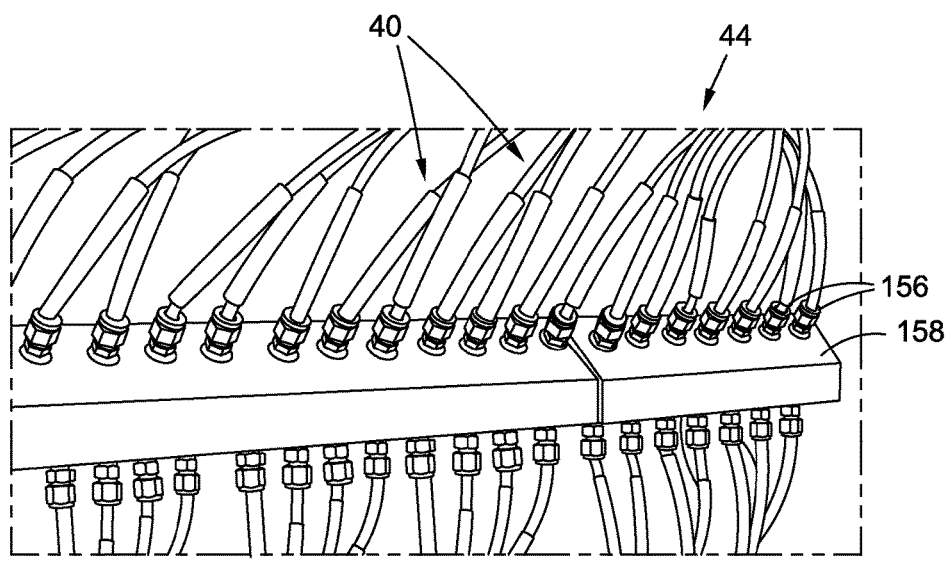
FIG. 6 is an illustration of a partial front perspective view of a drain manifold assembly of an embodiment of an oxygen analysis system (OAS) of the disclosure.

As shown in FIG. 1, the oxygen analysis system (OAS) 10 further comprises a drain manifold assembly 44 (see also FIG. 6). The drain manifold assembly 44 (see FIG. 1) is preferably coupled along the transport tubing assembly 40 (see FIG. 1) between the rack support structure 30 (see FIG. 1) and the plurality of fuel tank gas sampling ports 24 (see FIG. 1). The drain manifold assembly 44 (see FIG. 1) is preferably configured to capture and drain liquids that may enter into the transport tubing assembly 40 (see FIG. 1) and contaminate or interfere with the gas sample 70 (see FIG. 2).

Figure 5:
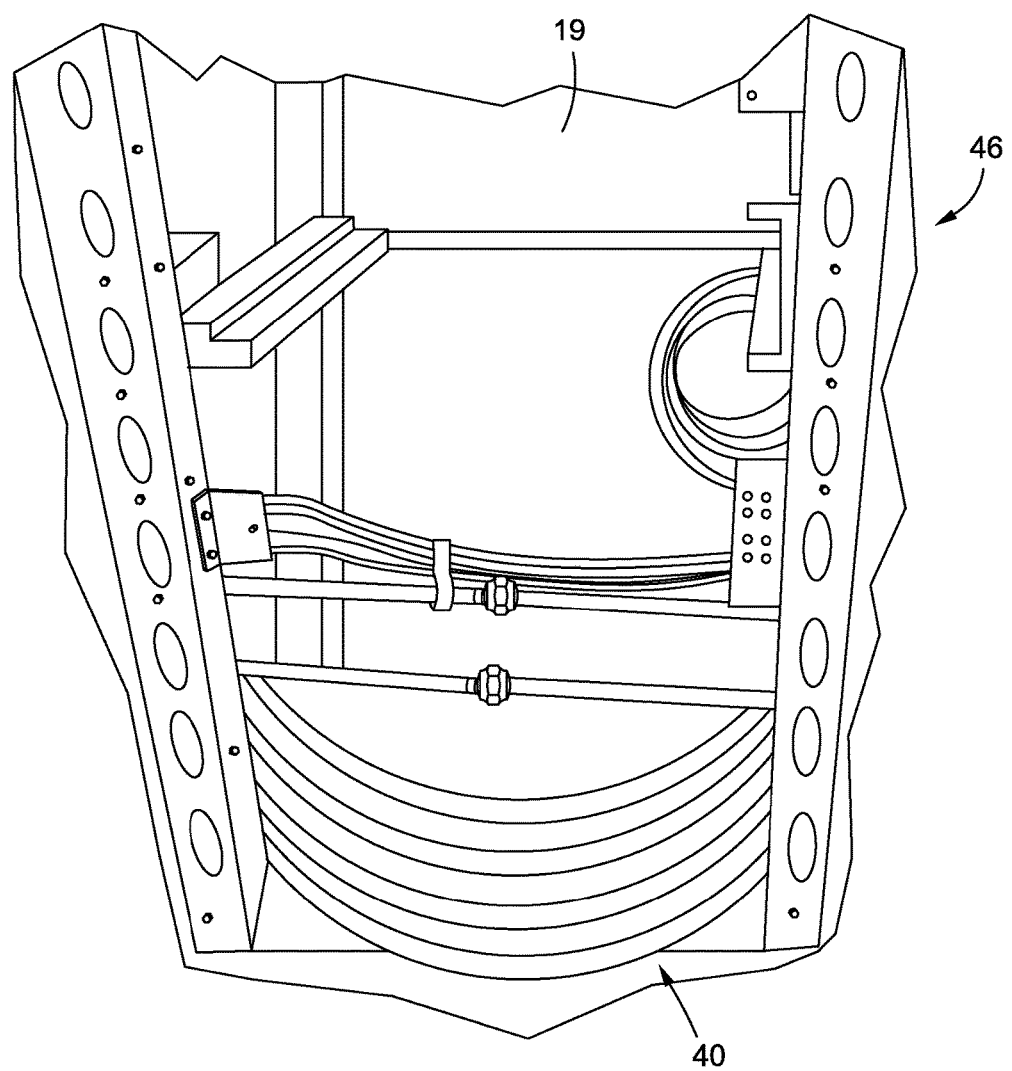
FIG. 5 is an illustration of a partial front perspective view of a transport tubing inspection point of an embodiment of an oxygen analysis system (OAS) of the disclosure.

As shown in FIG. 1, the oxygen analysis system (OAS) 10 further comprises a transport tubing inspection point 46 (see also FIG. 5). The transport tubing inspection point 46 is preferably located in the cargo bay 19 (see FIG. 1) of the aircraft 12 and is a low point inspection point for the transport tubing assembly 40 (see FIG. 2).

As shown in FIG. 1, the oxygen analysis system (OAS) 10 further comprises a data acquisition and recording system 50 coupled to the rack support structure 30 via a data connection 52. The data acquisition and recording system 50, such as in the form of flight test data acquisition and recording system 50a (see FIG. 1), is designed for collecting and processing oxygen concentration data 68 (see FIG. 2) measured by an oxygen sensor 64 (see FIG. 2), such as in the form of a tunable laser diode oxygen sensor 64a (see FIG. 2), of each oxygen analyzer device 34 (see FIG. 2). Preferably, the data acquisition and recording system 50 (see FIG. 1) comprises a user interface software 58 (see FIG. 2) to monitor and control the oxygen analysis system 10 (see FIG. 1).

Although the aircraft 12 shown in FIG. 1 is generally representative of a commercial passenger aircraft that may incorporation the OAS 10, the teachings of the disclosed embodiments of the OAS 10 and oxygen analysis method 200 may be equally applicable to other aerial vehicles such as cargo aircraft, military aircraft, rotorcraft, and other types of aircraft or aerial vehicles having fuel tanks for which oxygen concentration measurements may be required.

Figure 2:
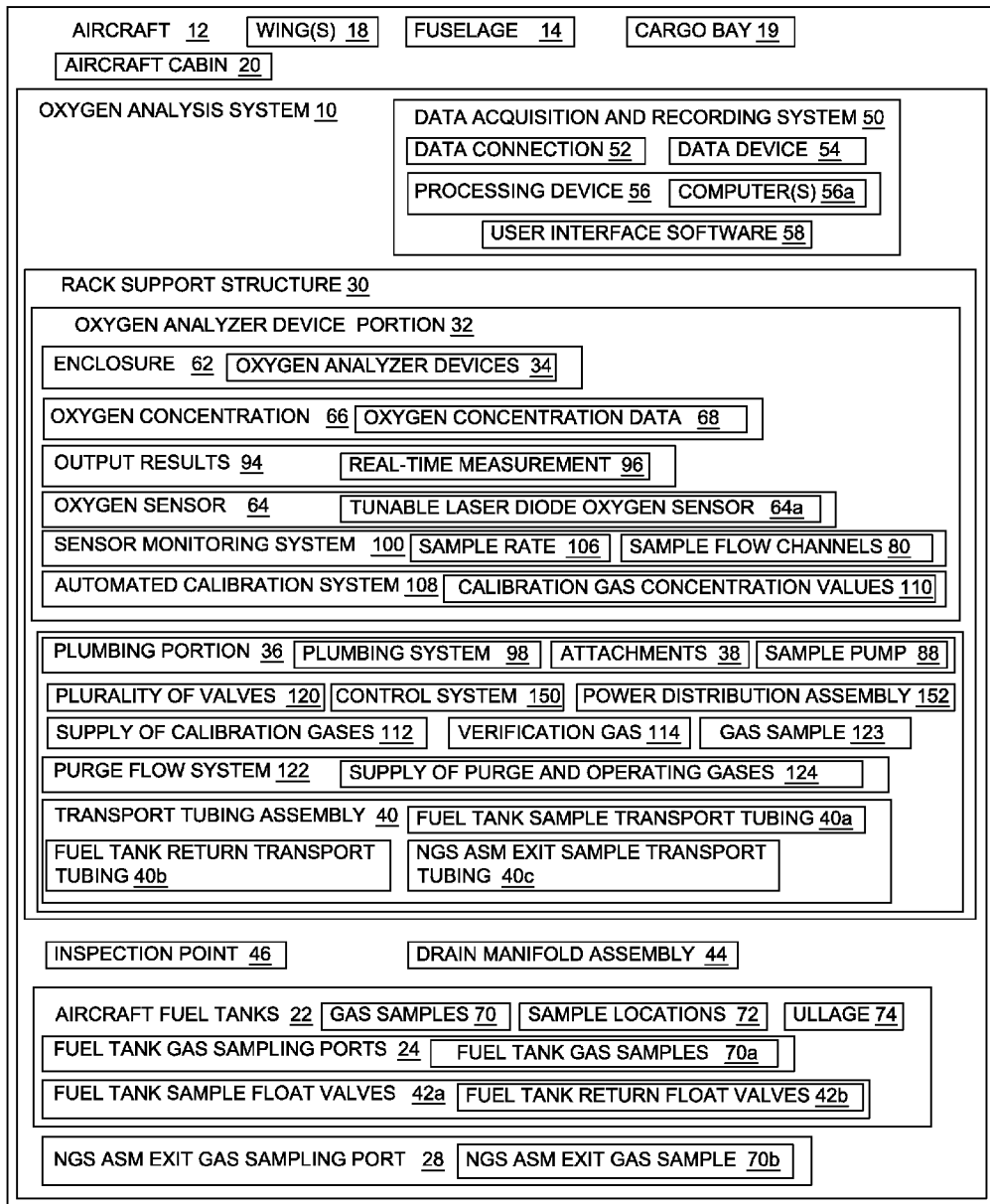
FIG. 2 is an illustration of a functional block diagram of an aircraft having an embodiment of an oxygen analysis system (OAS) of the disclosure.

FIG. 2 is an illustration of a functional block diagram of an aircraft 12 having an embodiment of an oxygen analysis system (OAS) 10 of the disclosure. In one embodiment of the disclosure, as shown in FIG. 2, there is provided an oxygen analysis system 10 for measuring, monitoring and recording oxygen concentration 66 in aircraft fuel tanks 22.

As shown in FIG. 2, the oxygen analysis system 10 comprises a rack support structure 30 (see also 4A-4D). The rack support structure 30 is preferably installed in the aircraft cabin 20 (see also FIG. 1).

Figure 3:
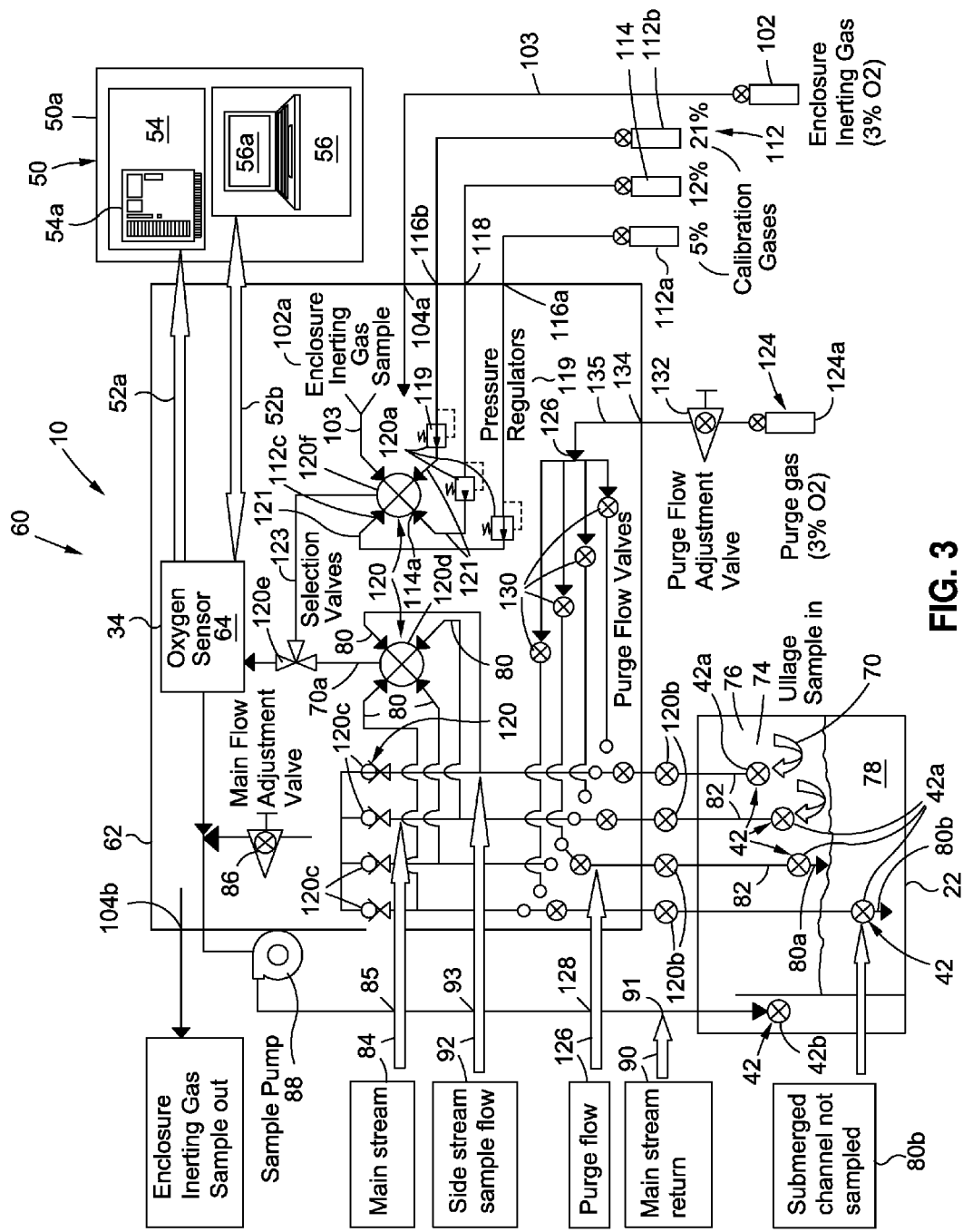
FIG. 3 is an illustration of a schematic diagram of an embodiment of an oxygen analysis system (OAS) process flow of the disclosure.
Figure 4A:
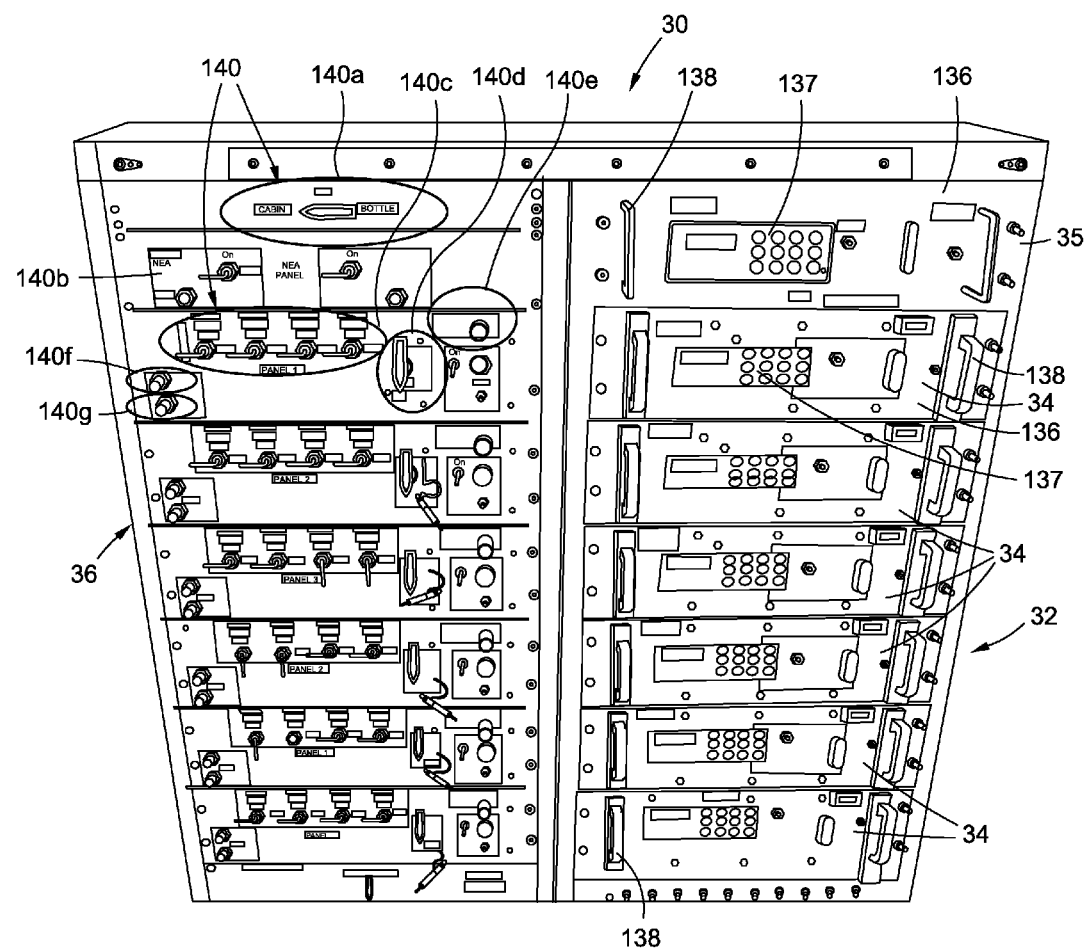
FIGS. 4A-4D are illustrations of perspective views of a rack support structure of an embodiment of an oxygen analysis system (OAS) of the disclosure.

The rack support structure 30 (see FIGS. 1, 2) preferably comprises the oxygen analyzer device portion 32 (see FIGS. 1, 2, 4A) and the plumbing portion 34 (see FIGS. 1, 2, 4A). The oxygen analyzer device portion 32 (see FIGS. 1, 2, 4A) comprises a plurality of oxygen analyzer devices 34 (see FIG. 2) mounted in the rack support structure 30 (see FIG. 4A). Each oxygen analyzer device 34 is preferably positioned in an enclosure 62 (see FIGS. 2, 3). As shown in FIG. 2, each oxygen analyzer device 34 comprises an oxygen sensor 64 to measure oxygen concentration 66 in gas samples 70 continuously drawn from sample locations 72 in aircraft fuel tanks 22 and also drawn at an aircraft nitrogen generation system (NGS) air separation module (ASM) exit 26 (see FIG. 1). Preferably, the oxygen sensor 64 (see FIG. 2) is a tunable laser diode oxygen sensor 64a (see FIG. 2).

The oxygen sensor 64 (see FIG. 2) preferably comprises laser diode absorption technology to measure oxygen concentration in the gas sample 70 (see FIG. 2). The laser diode produces light in the visible spectrum at 760 nanometers, which is absorbed by oxygen. To analyze oxygen, a laser beam is preferably focused through the gas sample 70 (see FIG. 2) onto a detector. The oxygen concentration may be inversely proportional to the amount of light reaching the detector. The laser diode of the tunable laser diode oxygen sensor 64a is preferably tuned to an absorption frequency of oxygen and an oxygen sensor signal strength is preferably proportional to an oxygen concentration in a gas sample 70 (see FIG. 2). An oxygen sensor 64, such as in the form of tunable laser diode oxygen sensor 64a (see FIG. 2), that may be used in the OAS 10 disclosed herein may be obtained from Oxigraf, Inc. of Mountain View, Calif.

As shown in FIG. 2, the oxygen analyzer device portion 32 may further comprise a sensor monitoring system 100 to monitor the oxygen sensor 64 of each oxygen analyzer device 34. Preferably, the sensor monitoring system 100 monitors the oxygen sensor 64 at a sample rate 106 equal to or greater than about one (1) sample per thirty (30) seconds per sample flow channel 80.

As shown in FIG. 2, the oxygen analyzer device portion 32 may further comprise an automated calibration system 108. The automated calibration system 108 preferably uses one or more calibration gas concentration values 110 obtained from a supply of calibration gases 112 to calibrate the oxygen analysis system 10 in real time. The calibration gases 112 (see FIGS. 2, 3) preferably comprise a low oxygen concentration calibration gas 112a (see FIG. 3) comprising an oxygen gas having a 5% oxygen concentration. The calibration gases 112 preferably further comprise a high oxygen concentration calibration gas 112b (see FIG. 3) comprising an oxygen gas having a 21% oxygen concentration. The automated calibration system 108 is preferably a 2-point calibration that uses precision calibration gases at 5% and 21%. By comparing what the oxygen sensor 64 measures versus a known oxygen concentration 66 (see FIG. 2) of a known calibration gas 112 (see FIG. 3), the oxygen sensor 64 may be calibrated to remove any error. The automated calibration system 108 may be used to ensure that the oxygen sensor 64 is producing a high level of quality oxygen concentration data 68 (see FIG. 2).

As further shown in FIG. 2, the plumbing portion 36 of the oxygen analysis system 10 comprises a plumbing system 98. The plumbing system 98 may comprise attachments 38 (see also FIG. 1) to the rack support structure 30 (see FIG. 1) and a sample pump 88 (see also FIG. 3). The sample pump 88 helps to circulate the sample flow through the plumbing system 98 and to the aircraft fuel tanks 22 (see FIG. 3).

As shown in FIG. 2, the plumbing portion 36 of the oxygen analysis system 10 further comprises a plurality of valves 120, a supply of calibration gases 112, a purge flow system 122 with a supply of purge and operating gases 124, a control system 150, and a power distribution assembly 152, all coupled to the rack support structure 30. The plurality of valves 120 (see FIGS. 2, 3) may comprise valves that help to stop, start, control or adjust the sample flow. For example, as shown in FIG. 3, the plurality of valves may be manual or automated and may comprise one or more pressure regulator valves 120a, manual control valves 120b, check valves 120c, and sectional valves 120d. Additional valves may include float valves 42 (see FIGS. 1, 3), such as fuel tank sample float valves 42a, main flow adjustment valve 86 (see FIG. 3), purge flow valves 130 (see FIG. 3), purge flow adjustment valve 132 (see FIG. 3).

Preferably, the plurality of valves 120 (see FIGS. 2, 3) is designed so that only one selection port is enabled at a given time. Preferably, the plurality of valves 120 of the OAS 10 has a binary tree arrangement.

The supply of purge and operating gases 124 (see FIG. 2) may comprise a purge gas 124a (see FIG. 2) preferably comprising an oxygen gas having a 3% oxygen concentration. The purge flow 126 (see FIG. 3) will be discussed in detail below with respect to FIG. 3.

The control system 150 (see FIG. 2) for the OAS 10 may provide varying levels of control depending on what components are operational in the OAS 10. For example, the control system 150 may enable or disable the plurality of valves 120 (see FIG. 2), in order to control and regulate, for example, the amount of sample flow, the temperature and pressure of the sample flow, and other applicable features. Further, the control system 150 may control and/or regulate the power distribution assembly 152, various switches (not shown), power lines (not shown), and other components of the OAS 10 (see FIG. 2). For example, the one or more control systems 150 (see FIG. 2) may comprise one or more of a pneumatic control system, a mechanical control system, a hydraulic control system, an electrical control system, or another suitable control system. The control system 150 preferably comprises controls that may be located in the aircraft cabin 20 with the data acquisition and recording system 50 (see FIG. 2) or in the flight deck or in another suitable location in the aircraft 12 (see FIG. 1). The control system 150 (see FIG. 1) and controls may be coupled to or connected to the OAS 10 (see FIG. 1) via one or more wired control lines (not shown) or via wireless couplings or connections (not shown).

The power distribution assembly 152 (see FIG. 2) for the OAS 10 (see FIG. 2) preferably provides power to one or more components of the OAS (see FIGS. 1-3). The power distribution assembly 152 (see FIG. 2) that drives one or more components of the OAS 10 (see FIG. 1) may comprise one or more of pneumatic power, electric power, hydraulic power, mechanical power, or another suitable form of power.

As shown in FIG. 2, the oxygen analysis system 10 (see FIG. 2) further comprises a transport tubing assembly 40 coupled between the rack support structure 30 and the aircraft fuel tanks 22 and the NGS ASM exit 26 (see FIG. 1). The transport tubing assembly 40 is configured to transport the gas samples 70 to and from the plurality of oxygen analyzer devices 34 in the rack support structure 30. As shown in FIGS. 1 and 2, the transport tubing assembly 40 preferably comprises fuel tank sample transport tubing 40*a*, fuel tank return transport tubing 40*b*, and NGS ASM exit sample transport tubing 40*c*.

As shown in FIG. 2, the oxygen analysis system 10 (see FIG. 2) further comprises a drain manifold assembly 44 (see FIGS. 1, 2, 6) coupled along the transport tubing assembly 40 (see FIG. 1) between the rack support structure 30 (see FIG. 1) and the aircraft fuel tanks 22 (see FIG. 1), including the plurality of fuel tank gas sampling ports 24 (see FIG. 1). The drain manifold assembly 44 (see FIGS. 1, 2, 6) is preferably configured to capture and drain liquids, such as liquid fuel 78 (see FIG. 3) that may inadvertently enter into the transport tubing assembly 40.

As shown in FIG. 2, the oxygen analysis system 10 (see FIG. 2) further comprises a transport tubing inspection point 46 (see also FIGS. 1, 5). The transport tubing inspection point 46 is preferably located in the cargo bay 19 (see FIG. 1) of the aircraft 12 and is a low point inspection point for the transport tubing assembly 40 (see FIG. 2).

As shown in FIG. 2, the oxygen analysis system 10 (see FIG. 2) further comprises a plurality of fuel tank gas sampling ports 24 (see also FIG. 1) located in the aircraft fuel tanks 22. Gas samples 70 (see FIG. 2), such as fuel tank gas samples 70*a* (see FIG. 2) are preferably drawn from multiple sample locations 72 (see FIG. 2) in the aircraft fuel tanks 22 (see FIG. 2). Preferably, the plurality of fuel tank gas sampling ports 24 comprise up to twenty-one (21) sample locations 72 (see FIG. 2) in the aircraft fuel tanks 22. However, more or less than twenty-one (21) sample locations 72 (see FIG. 2) may also be used.

Preferably, the gas samples 70 (see FIG. 2) drawn from the sample locations 72 within the aircraft fuel tanks 22 are drawn from an ullage 74 (see FIGS. 2, 3) of each aircraft fuel tank 22. For purposes of this application, "ullage" means the unfilled space 76 (see FIG. 3) in the aircraft fuel tank 22 (see FIG. 3) above a liquid fuel 78 (see FIG. 3).

The oxygen analysis system 10 (see FIG. 2) further comprises an NGS ASM exit gas sampling port 28 (see FIG. 2) located at the NGS ASM exit 26 (see FIG. 1). The gas sample 70 (see FIG. 2), such as NGS ASM exit gas sample 70*b* (see FIG. 2), is preferably drawn from the NGS ASM exit 26 (see FIG. 1).

The oxygen analysis system 10 further comprises a data acquisition and recording system 50 (see FIG. 2) coupled to the plurality of oxygen analyzer devices 34 via the data connection 52 (see FIG. 2), for collecting and processing output results 94 (see FIG. 2) and real-time measurement 96 (see FIG. 2) from the oxygen analyzer device 34 (see FIG. 2), of, for example, oxygen concentration data 68 (see FIG. 2) measured by the oxygen sensor 64 (see FIG. 2) of each oxygen analyzer device 34 (see FIG. 2).

As shown in FIG. 2, the data acquisition and recording system 50 comprises a data device 54. The data device 54 preferably comprises a data acquisition and recording device 54*a* (see FIG. 3) and may comprise storage media, recording media, and other suitable devices. The data acquisition and recording system 50 (see FIG. 2) preferably collects, stores and processes oxygen concentration data 68 (see FIG. 2) acquired by the oxygen sensor 64 (see FIG. 2) of the oxygen analyzer device 34 to obtain an oxygen concentration profile for the aircraft fuel tanks 22.

As shown in FIG. 2, the data acquisition and recording system 50 further comprises a processing device 56 (see FIG. 2), such as in the form of one or more computers 56*a* (see FIG. 2) with associated user interface software 58 (see FIG. 2). For example, the processing device may include system memory, an operating system, applications, input/output devices, input/output interfaces, or other suitable processing devices. The data acquisition and recording system 50 (see FIG. 2) further comprises a user interface software 58 (see FIG. 2) to monitor and control the oxygen analysis system 10. The OAS 10 (see FIG. 20 is preferably automated and may be controlled by the user interface software 58 (see FIG. 2).

The user interface software 58 (see FIG. 2) preferably offers a user or an operator a series of displays, such as, the sample flow channel 80 (see FIG. 2) being sampled at a given point in time, the oxygen concentration level of the gas sample, and identifies the oxygen sensor 64 (see FIG. 2) flow rate sensor and pressure levels to determine whether or not the oxygen analyzer device 34 is receiving a suitable sample flow or whether or not there may be blockage in a transport tubing line.

Preferably, the user interface software 58 (see FIG. 2) is an automated user interface and is a flight-test-developed Labview application. The user interface software 58 (see FIG. 2) provides an operator-selectable channel scan configuration that may vary with fuel load, a real-time calibration and verification feature, and a stand-by capability to preserve consumable gases or to pause sampling during maneuvering flight where sampling ports might submerge FIG. 3 is an illustration of a schematic diagram of an embodiment of an oxygen analysis system (OAS) process flow 60 of the disclosure. FIG. 3 shows the various sample flows entering and exiting the oxygen analyzer device 34 and enclosure 62.

As shown in FIG. 3, the data connection output 52*a* may be sent to the data device 54, such as in the form of data acquisition and recording device 54*a*, of the data acquisition and recording system 50. Preferably, the data connection output 52*a* is transmitted via a communication protocol, such as ARINC 429. Preferably, the data acquisition and recording device 54*a* comprises a flight test data system for post-flight data analysis. As further shown in FIG. 3, the data connection input/output 52*b* may be sent between the oxygen sensor 64 and the processing device 56 of the data acquisition and recording system 50. Preferably, the data connection input/output 52*b* is transmitted via a communication protocol, such as RS232.

FIG. 3 shows the oxygen analyzer device 34 with the oxygen sensor 64 in relation to the float valves 42, such as the fuel tank sample float valves 42*a*, in the aircraft fuel tank 22. FIG. 3 shows gas samples 70, such as fuel tank gas samples 70*a*, being drawn from the ullage 74, present in the unfilled space 76 in the aircraft fuel tank 22. The aircraft fuel tank 22 (see FIG. 3) also shows liquid fuel 78 (see FIG. 3) in the lower half of the aircraft fuel tank 22.

As further shown in FIG. 3, the ullage 74 sample is drawn into float valves 42, such as the fuel tank sample float valves 42*a*. If a float valve 42 is not submerged in the liquid fuel 78 (see FIG. 3) of the fuel tank 22 (see FIG. 3) and is above the liquid fuel 78, the unsubmerged channel 80*a* is sampled and drawn in by sense tubes 82 leading to the sample flow channels 80. Preferably, the sense tubes 82 are made of a strong, hydrophobic material such as polytetrafluoroethylene (PTFE) or another suitably strong, hydrophobic material. At the end of each sense tube 82 (see FIG. 3) is a float valve 42 (see FIG. 3). If the float valve 42 (see FIG. 3) is submerged in the liquid fuel 78 (see FIG. 3) of the fuel tank 22 (see FIG. 3), the submerged channel 80*b* is not sampled.

As shown in FIG. 3, each oxygen analyzer device 34 preferably has four sample flow channels 80 for oxygen concentration measurement. The gas sample 70, such as in the form of fuel tank gas sample 70*a*, flows continuously in a continuous loop from the aircraft fuel tank 22 through the fuel tank sample transport tubing 40a (see FIG. 1) to the oxygen sensor 64 of the oxygen analyzer device 34. The gas samples 70 are analyzed from one sample flow channel 80 to the next sample flow channel 80, so that all four sample flow channels 80 with fuel tank gas samples 70a are each individually analyzed. A selection valve 120d may be used to select the fuel tank gas sample 70a to be analyzed and a flow control valve 120e may be used to control the flow of the fuel tank gas sample 70a to the oxygen sensor 64. Once the gas sample 70 is analyzed, it is returned back to the aircraft fuel tank 22 it came from and is returned back via the fuel tank return transport tubing 40b (see FIG. 1).

As further shown in FIG. 3, a main stream sample flow 84 may enter the enclosure 62 through entry point 85. The main stream sample flow 84 preferably has a flow rate of about 500 ml/min (milliliters per minute) or another suitable flow rate. The main stream sample flow 84 (see FIG. 3) may flow past check valves 120c (see FIG. 3), past main flow adjustment valve 86, and out of the enclosure 62 through sample pump 88 to become a main stream return flow 90 (see FIG. 3). The main stream return flow 90 (see FIG. 3) returns via fuel tank return transport tubing 40b (see FIG. 1) back to the aircraft fuel tank 22 (see FIG. 3), and enters back in via entry point 91. The main stream return flow 90 (see FIG. 3) preferably has a flow rate of about 2000 ml/min (milliliters per minute) or another suitable flow rate. A predetermined amount of the main stream sample flow 84 may also be tapped off to flow to the oxygen sensor 64 via a side stream sample flow 92.

As further shown in FIG. 3, the side stream sample flow 92 may enter the enclosure 62 through entry point 93. The side stream sample flow 92 preferably has a flow rate of about 200 ml/min (milliliters per minute) or another suitable flow rate. The side stream sample flow 92 (see FIG. 3) may flow through selection valves 120d (see FIG. 3), and to the oxygen sensor 64 (see FIG. 3).

As discussed above, the OAS 10 may comprise a sensor monitoring system 100 to monitor, such as to self-monitor, the oxygen sensor 64 of each oxygen analyzer device 34. To ensure that an oxygen concentration 66 (see FIG. 2) level inside the enclosure 62 is below a level that may be flammable if there is a fuel leakage within the enclosure 62 and if there is a fuel ignition source present to prevent ignition, it is preferable that the enclosure 62 have a low oxygen concentration.

The oxygen sensor 64 (see FIG. 3) may be set by the user interface software 58 (see FIG. 2) to measure its own enclosure 62 atmosphere or oxygen concentration 66 (see FIG. 2) and to verify that the enclosure 62 is maintained at an oxygen concentration 66 (see FIG. 2) below a flammable level to allow the OAS 10 to be installed and flown on the aircraft 12 (see 1).

Sampling an internal gas environment or atmosphere of the enclosure 62 (see FIG. 3) for the oxygen sensor 64 involves using a gas sample 123 (see FIG. 3). A user or operator of the OAS 10 may conduct a cyclical sampling by drawing several gas samples 70 (see FIG. 2) from the aircraft fuel tanks 22, and then switching and drawing a gas sample 70 (see FIG. 2) from the atmosphere in the enclosure 62 (see FIG. 3), and the switching back again. The sampling of the atmosphere in the enclosure 62 (see FIG. 3) involves switching the plurality of valves 120 (see FIGS. 2, 3) at the appropriate rate to periodically monitor the oxygen concentration 66 (see FIG. 2) of the enclosure 62 (see FIG. 2) and the user interface software 58 (see FIG. 2) detects if the oxygen concentration 66 (see FIG. 2) of the enclosure 62 (see FIG. 2) goes above a certain threshold value. If the oxygen concentration 66 (see FIG. 2) of the enclosure 62 (see FIG. 2) goes above the threshold value, the user interface software 58 (see FIG. 2) preferably alerts the user or operator that the enclosure 62 (see FIG. 2) is not maintaining an inert environment or atmosphere within the enclosure 62.

The OAS 10 may further comprise an enclosure inerting gas 102 (see FIG. 3) comprising an oxygen gas preferably having a 3% oxygen concentration. The enclosure inerting gas 102 (see FIG. 3) may be used to maintain the atmosphere of the enclosure 62 (see FIG. 3) of each oxygen analyzer device 34 (see FIG. 3) at preferably less than 12% oxygen concentration, and more preferably at about 7% oxygen concentration, throughout an aircraft flight duration. The oxygen concentration may be adjustable by a user. The enclosure inerting gas 102 preferably having a 3% oxygen concentration may be added as needed to keep the atmosphere of the enclosure 62 at an acceptable level.

As shown in FIG. 3, the sensor monitoring system 100 uses the enclosure inerting gas 102 preferably comprising oxygen gas having a 3% oxygen concentration. FIG. 3 shows an enclosure inerting gas sample flow channel 103 entering the enclosure 62 through entry point 104a. Once through the entry point 104a, as shown in FIG. 3, the enclosure inerting gas 102 flows through the enclosure inerting gas sample flow channel 103 to a selection valve 120f. The selection valve 120f may be used to select the enclosure inerting gas 102 as a sample to be analyzed by the oxygen sensor 64, and the flow control valve 120e may be used to control the flow of the enclosure inerting gas 102 to the oxygen sensor 64. Once the enclosure inerting gas sample 102a is analyzed by the oxygen sensor 64, the enclosure inerting gas sample 102a exits the enclosure 62 through exit point 104b.

As discussed above, the OAS 10 may comprise an automated calibration system 108. As shown in FIG. 3, the supply of calibration gases 112 to calibrate the OAS 10 in real time includes a low oxygen concentration calibration gas 112a comprising an oxygen gas having a 5% oxygen concentration and further comprises a high oxygen concentration calibration gas 112b comprising an oxygen gas having a 21% oxygen concentration.

As further shown in FIG. 3, the oxygen analysis system 10 may further comprise a verification gas 114. Preferably, the verification gas 114 comprises an oxygen gas having a 12% oxygen concentration may also be used with the automated calibration system 108.

As shown in FIG. 3, the calibration gases 112 enter the enclosure 62 through entry points 116a, 116b, respectively. As further shown in FIG. 3, the verification gas 114 enter the enclosure 62 through entry point 118. Once in the enclosure 62, the calibration gases 112a, 112b and the verification gas 114 flow through a plurality of pressure regulators 119 with pressure regulator valves 120a to the selection valve 120f. The selection valve 120f may be used to select one of the calibration gases 112a, 112b or the verification gas 114 (or the enclosure inerting gas 102) as a gas sample 123 to be analyzed by the oxygen sensor 64, and the flow control valve 120e may be used to control the flow of the selected gas sample 123 to the oxygen sensor 64.

The gas sample 123 may comprise a calibration gas sample 112c (see FIG. 3), a verification gas sample 114a (see FIG. 3), or an enclosure inerting gas sample 102a (see FIG. 3), for example, an NGS ASM exit gas sample 70b (see FIG.

2). Once the gas sample 123 is analyzed by the oxygen sensor 64, they exit the sensor 64 and may exit the enclosure 62.

In addition to the control valve 120e (see FIG. 3) controlling the flow of the fuel tank gas sample 70a (see FIG. 3) selected by the selection valve 120d (see FIG. 3), the control valve 120e controls the flow of the gas sample 123 (see FIG. 3) selected by the selection valve 120f (see FIG. 3). The control valve 120e controls which sample, i.e., a fuel tank gas sample 70a or a gas sample 123, is selected to flow into the oxygen sensor 64 for analysis.

As discussed above, the OAS 10 may comprise a purge flow system 122 (see FIG. 2). As shown in FIG. 3, a supply of purge and operating gases 124 may be used. The supply of purge and operating gases 124 (see FIG. 3) preferably comprises a purge gas 124a (see FIG. 3) comprising an oxygen gas having a 3% oxygen concentration. The purge gas 124a may be used to control the plurality of valves 120 (see FIGS. 2, 3) and may be used to provide a purge capability in real time to clear any blocked sample flow channels 80 (see FIG. 3) of the transport tubing assembly 40 (see FIG. 2).

As shown in FIG. 3, a purge flow 126 enters the enclosure 62 through entry point 128 and may flow through the sample flow channels 80 to purge the sample flow channels 80 of any blockages. As further shown in FIG. 3, the purge gas 124a flows past the purge flow adjustment valve 132 and into the enclosure 62 through entry point 134. The purge gas 124a (see FIG. 3) may then flow past the purge flow valves 130 and may also flow through the sample flow channels 80 to purge the sample flow channels 80 of any blockages. Thus, the purge flow system 122 (see FIG. 2) provides automatic and manual purge (back-flow) capability to clear blocked sample flow channels 80 using 3% purge (and valve control) gas 124a (see FIG. 3).

FIGS. 4A-4D are illustrations of perspective views of the rack support structure 30 of an embodiment of the oxygen analysis system (OAS) 10 of the disclosure. FIG. 4A shows a front view of the rack support structure 30 with the oxygen analyzer device portion 32 on the right and the plumbing portion 36 on the left. As shown in FIG. 4A, the oxygen analyzer device portion 32 comprises a plurality of oxygen analyzer devices 34 and a nitrogen-enriched air (NEA) analyzer device 35 mounted in the rack support structure 30. FIG. 4A shows the oxygen analyzer device portion 32 comprising in one embodiment six (6) oxygen analyzer devices 34 and one NEA analyzer device 35 stacked vertically within the rack support structure 30. The oxygen analyzer devices 34 and the NEA analyzer device 35 each have an exterior face 136, a control panel 137, and a set of handles 138 for pulling the oxygen analyzer device 34 or the NEA analyzer device 35 out of the rack support structure 30.

FIG. 4A further shows the plumbing portion 36 with a plurality of plumbing system control displays 140. As shown in FIG. 4A, the plurality of plumbing system controls 140 may include such controls as a verification gas control 140a, an NGS ASM exit gas sampling port control 140b, fuel tank gas sample line controls 140c, a return flow control 140d, a purge flow adjustment valve control 140e, an inlet test port control 140f, and a return test port control 140g, and may also include other suitable controls.

Figure 4B:
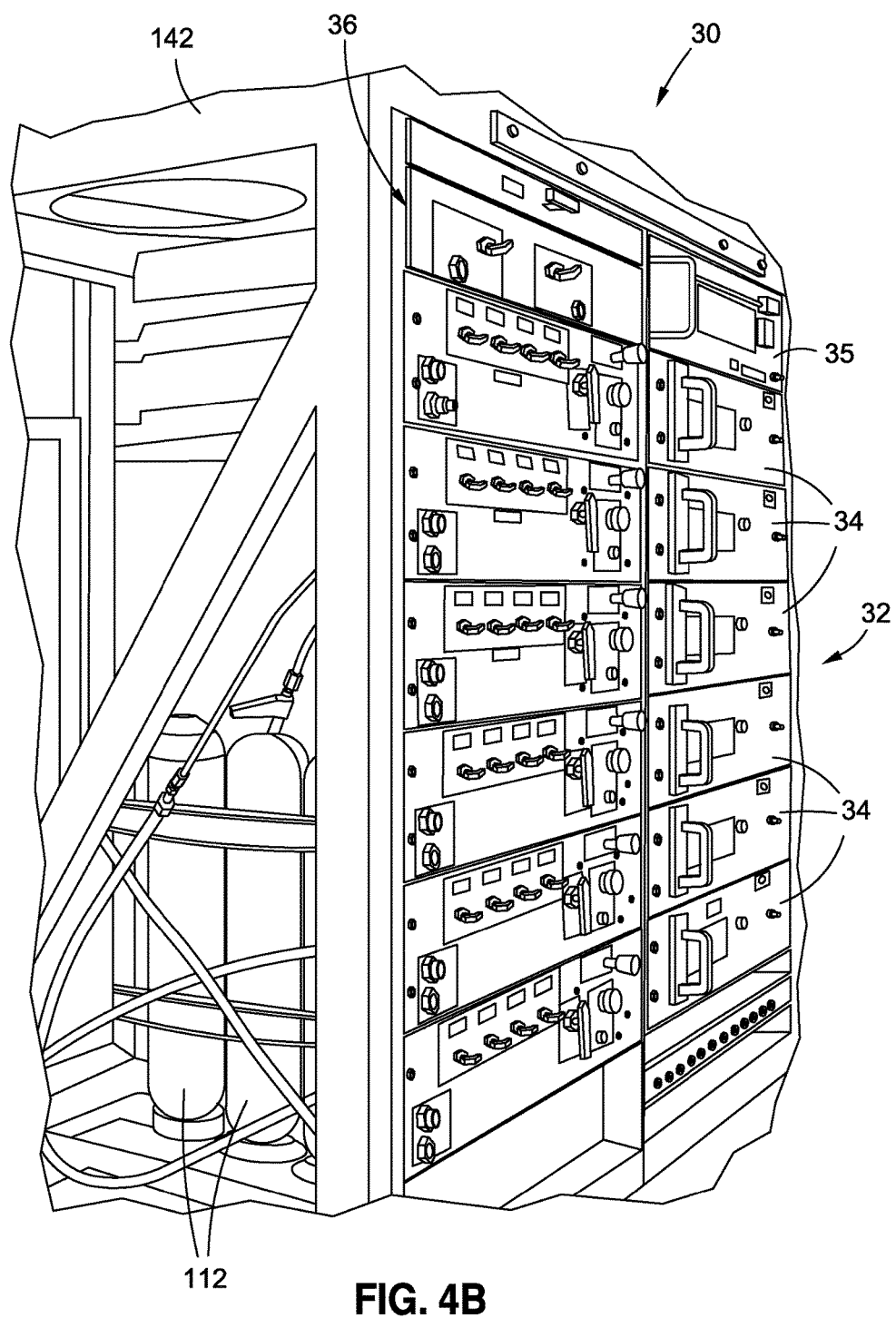

FIG. 4B shows a side perspective view of the rack support structure 30. FIG. 4B shows the oxygen analyzer device portion 32 with the plurality of oxygen analyzer devices 34 and the nitrogen-enriched air (NEA) analyzer device 35. FIG. 4B further shows the plumbing portion 36. As shown in FIG. 4B, an open side 142 of the rack support structure 30 shows a supply of calibration gases 112 housed within the rack support structure 30 behind the plumbing portion 36.

Figure 4C:
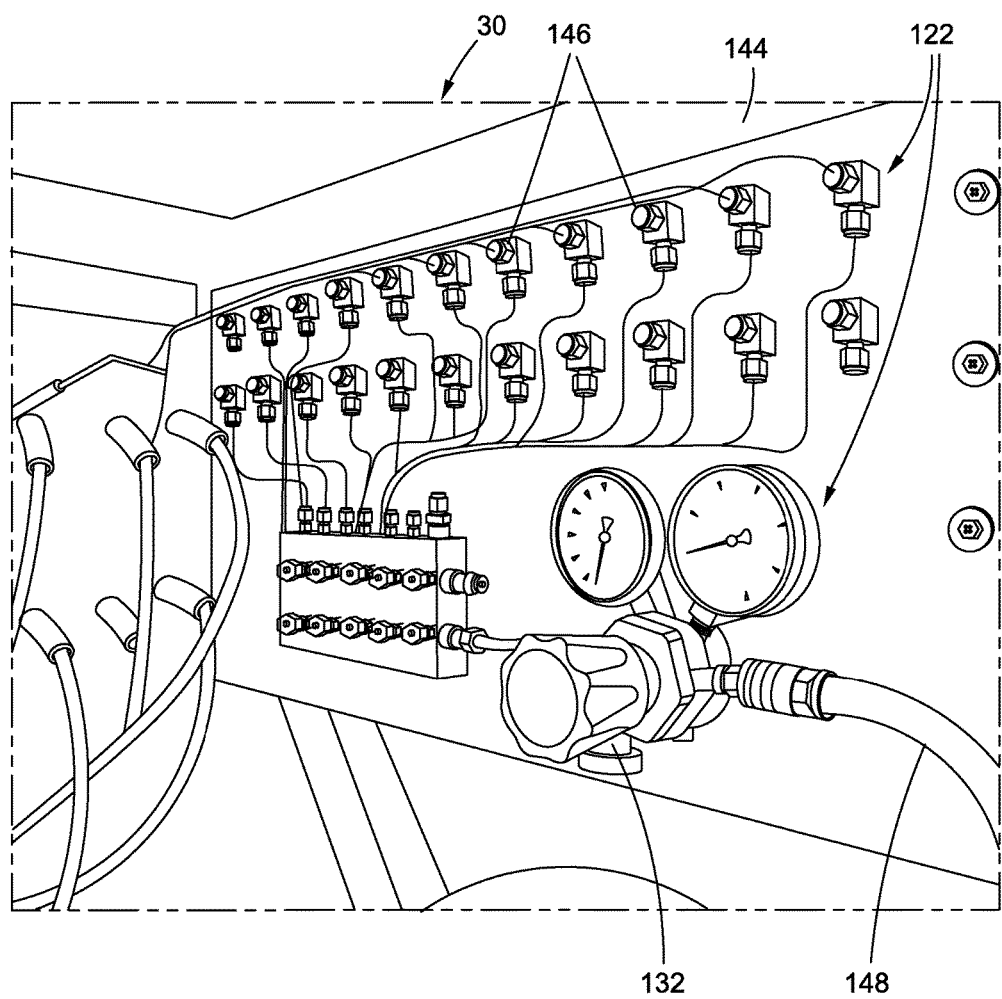

FIG. 4C shows an interior 144 of the rack support structure 30. FIG. 4C further shows the purge flow system 122 with purge flow system controls 146. The purge flow system controls 146 are preferably rack mounted through the rack support structure 30. FIG. 4C further shows the purge flow adjustment valve 132 coupled to a purge flow line 148.

Figure 4D:
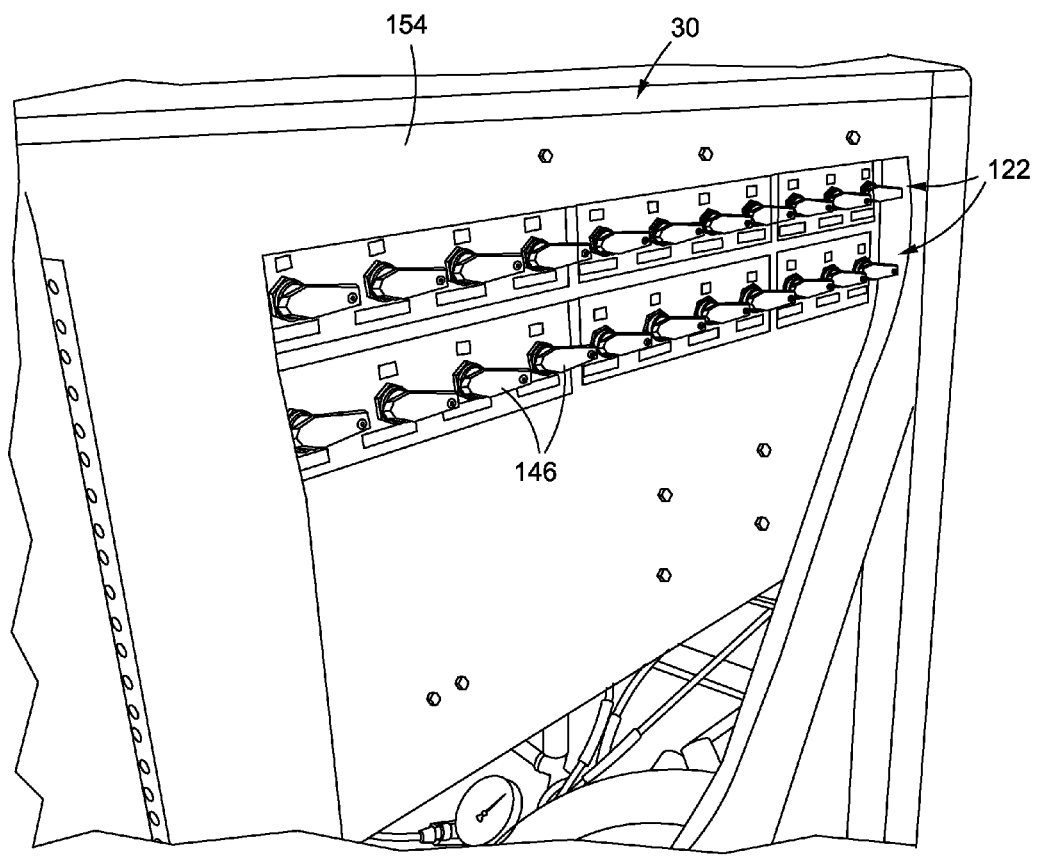

FIG. 4D shows an exterior 154 of the rack support structure 30. FIG. 4D further shows the purge flow system 122 with purge flow system controls 146. The purge flow system controls 146b are preferably rack mounted through the rack support structure 30 from the interior 144 (see FIG. 4C).

Figure 4E:
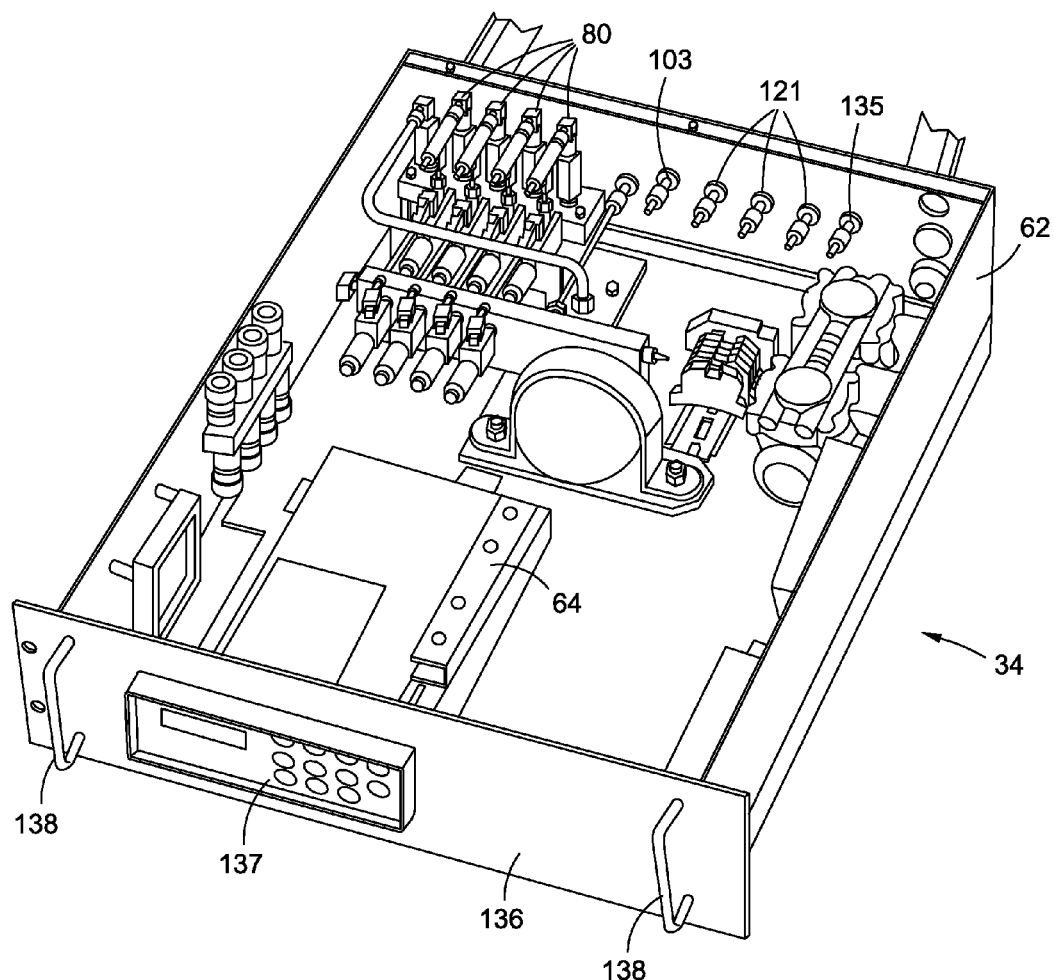
FIG. 4E is an illustration of a top perspective view of an oxygen analyzer device of an embodiment of an oxygen analysis system (OAS) of the disclosure.

FIG. 4E is an illustration of a top perspective view of an oxygen analyzer device 34 of an embodiment of the oxygen analysis system (OAS) 10 of the disclosure. FIG. 4E shows the enclosure 62 of the oxygen analyzer device 34. FIG. 4E further shows the oxygen sensor 64, the sample flow channels 80, the enclosure inerting gas sample flow channel 103, the calibration gas sample flow channels 121, and the purge flow channel 135. FIG. 4E further shows the exterior face 136, the control panel 137, and the set of handles 138 of the oxygen analyzer device 34.

FIG. 5 is an illustration of a partial front perspective view of the transport tubing inspection point 46 (see also FIG. 1) of an embodiment of the oxygen analysis system (OAS) 10 of the disclosure. FIG. 5 shows the transport tubing assembly 40 and transport tubing inspection point 46 located in the cargo bay 19 of an aircraft 12 (see FIG. 1).

FIG. 6 is an illustration of a partial front perspective view of the drain manifold assembly 44 of an embodiment of the oxygen analysis system (OAS) 10 of the disclosure. FIG. 6 shows the transport tubing assembly 40 with connection ports 156 attached to a manifold 158. The drain manifold assembly 44 is designed to capture or trap any unwanted liquids, such as liquid fuel 78 (see FIG. 3) that may inadvertently enter the transport tubing assembly 40.

In another embodiment of the disclosure, there is provided an aircraft 12 (see FIGS. 1, 2) having at least one wing 18 (see FIGS. 1, 2), each wing 18 having one or more aircraft fuel tanks 22 (see FIGS. 1, 2). The aircraft 12 (see FIGS. 1, 2) further comprises a fuselage 14 (see FIGS. 1, 2) defining an interior aircraft cabin 20 (see FIGS. 1, 2). The aircraft 12 (see FIGS. 1, 2) further comprises an oxygen analysis system (OAS) 10, as discussed in detail above.

The OAS 10 (see FIGS. 1, 2) of the aircraft 12 (see FIGS. 1, 2) comprises a rack support structure 30 (see FIGS. 2, 4A) installed in the aircraft cabin 20 (see FIG. 1). The OAS 10 (see FIGS. 1, 2) further comprises a plurality of oxygen analyzer devices 34 (see FIGS. 2, 4A) mounted in the rack support structure 30 (see FIGS. 2, 4A). Each oxygen analyzer device 34 comprises a tunable laser diode oxygen sensor 64a (see FIG. 2) to measure oxygen concentration 66 (see FIG. 2) in gas samples 70 (see FIG. 2) continuously drawn from sample locations 72 (see FIG. 2) in aircraft fuel tanks 22 (see FIG. 2) and at an aircraft nitrogen generation system (NGS) air separation module (ASM) exit 26 (see FIG. 1).

The OAS 10 (see FIG. 2) of the aircraft 12 (see FIG. 2) further comprises a plurality of valves 120 (see FIG. 2), a supply of calibration gases 112 (see FIG. 2), a purge flow system 122 (see FIG. 2) with a supply of purge and operating gases 124 (see FIG. 2), and a power distribution assembly 152 (see FIG. 2), all coupled to the rack support structure 30 (see FIG. 2). The OAS 10 (see FIG. 2) of the aircraft 12 (see FIG. 2) further comprises a transport tubing assembly 40

(see FIG. 2) coupled between the rack support structure 30 (see FIG. 2) and the aircraft fuel tanks 22 (see FIG. 2) and the NGS ASM exit 26 (see FIG. 1). The transport tubing assembly 40 is configured to transport the gas samples 70 (see FIG. 2) to and from the plurality of oxygen analyzer devices 34 (see FIG. 2) in the rack support structure 30 (see FIG. 2).

The OAS 10 (see FIG. 2) of the aircraft 12 (see FIG. 2) further comprises a plurality of fuel tank gas sampling ports 24 (see FIG. 2) located in the aircraft fuel tanks 22 (see FIG. 2) and an NGS ASM exit gas sampling port 28 (see FIG. 2) located at the NGS ASM exit 26 (see FIG. 1). The OAS 10 (see FIG. 2) of the aircraft 12 (see FIG. 2) further comprises a drain manifold assembly 44 (see FIG. 2) coupled along the transport tubing assembly 40 (see FIG. 2) between the rack support structure 30 (see FIG. 2) and the plurality of fuel tank gas sampling ports 24 (see FIG. 2) and configured to capture and drain liquids that enter into the transport tubing assembly 40 (see FIG. 2).

The OAS 10 (see FIG. 2) further comprises a data acquisition and recording system 50 (see FIG. 2) coupled to the plurality of oxygen analyzer devices 34 (see FIG. 2), for collecting and processing oxygen concentration data 68 (see FIG. 2) measured by the tunable laser diode oxygen sensor 64a (see FIG. 2) of each oxygen analyzer device 34 (see FIG. 2). The data acquisition and recording system 50 (see FIG. 2) comprises a user interface software 58 (see FIG. 2) to monitor and control the OAS 10 (see FIG. 2). The OAS 10 (see FIG. 2) measures, monitors and records in real time an oxygen concentration 66 (see FIG. 2) in the aircraft fuel tanks 22 (see FIG. 2).

The OAS 10 (see FIG. 2) of the aircraft 12 (see FIG. 2) may further comprise a sensor monitoring system 100 (see FIG. 2) to monitor the oxygen sensor 64 (see FIG. 2) of each oxygen analyzer device 34 (see FIG. 2) at a sample rate 106 (see FIG. 2) equal to or greater than about one (1) sample per thirty (30) seconds per sample flow channel 80 (see FIG. 2). The OAS 10 (see FIG. 2) of the aircraft 12 (see FIG. 2) may further comprise an automated calibration system 108 (see FIG. 2) using one or more calibration gas concentration values 110 (see FIG. 2) obtained from the supply of calibration gases 112 (see FIG. 2) to calibrate the OAS 10 (see FIG. 2) in real time. The OAS 10 (see FIG. 2) of the aircraft 12 (see FIG. 2) may further comprise an enclosure inerting gas 102 (see FIG. 3) and a purge gas 124a (see FIG. 3), both comprising an oxygen gas having a 3% oxygen concentration.

Figure 7:
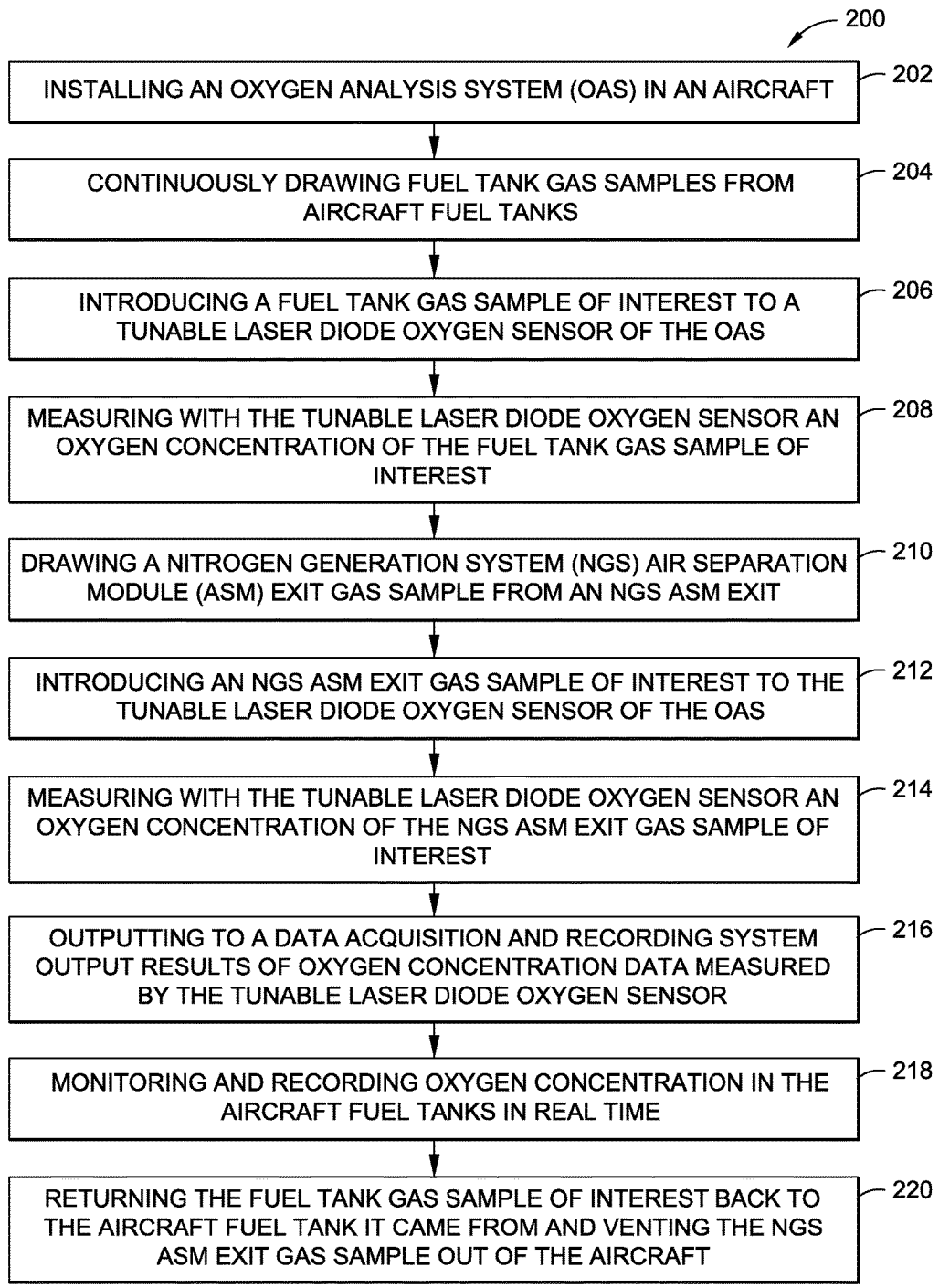
FIG. 7 is an illustration of a flow diagram showing an embodiment of an oxygen analysis method of the disclosure.

In another embodiment of the disclosure, there is provided an oxygen analysis method 200 for measuring, monitoring and recording oxygen concentrations 66 (see FIG. 2) in aircraft fuel tanks 22 (see FIG. 2). FIG. 7 is an illustration of a flow diagram showing an embodiment of the oxygen analysis method 200 of the disclosure.

As shown in FIG. 7, the oxygen analysis method 200 method comprises step 202 of installing the oxygen analysis system (OAS) 10, as discussed in detail above, in an aircraft 12. The step 202 of installing the OAS 10 (see FIG. 2) in the aircraft 12 (see FIG. 2) comprises installing the OAS 10 (see FIG. 2) comprising a rack support structure 30 (see FIG. 2) installed in an aircraft cabin 20 (see FIG. 1). The OAS 10 (see FIG. 2) further comprises a plurality of oxygen analyzer devices 34 (see FIG. 2) mounted in the rack support structure 30 (see FIG. 2). Each oxygen analyzer device 34 comprises a tunable laser diode oxygen sensor 64a (see FIG. 2).

The OAS 10 (see FIG. 2) further comprises a plurality of valves 120, a supply of calibration gases 112, a purge flow system 122 (see FIG. 2) having a supply of purge and operating gases 124 (see FIG. 2), and a power distribution assembly 152 (see FIG. 2), all coupled to the rack support structure 30 (see FIG. 2). The OAS 10 (see FIG. 2) further comprises a plurality of fuel tank gas sampling ports 24 (see FIG. 1) located in the aircraft fuel tanks 22 (see FIG. 1).

The OAS 10 (see FIG. 2) further comprises an aircraft nitrogen generation system (NGS) air separation module (ASM) exit gas sampling port 28 (see FIG. 1) located at the NGS ASM exit 26 (see FIG. 1). The OAS 10 (see FIG. 1) further comprises a transport tubing assembly 40 (see FIG. 1) coupled between the rack support structure 30 (see FIG. 1) and the fuel tank gas sampling ports 24 (see FIG. 1) and the NGS ASM exit gas sampling port 28 (see FIG. 1). The OAS 10 (see FIG. 1) further comprises a drain manifold assembly 44 (see FIG. 2) coupled to the transport tubing assembly 40 (see FIG. 2).

The OAS 10 (see FIG. 1) further comprises the data acquisition and recording system 50 (see FIG. 1), discussed above, coupled to the plurality of oxygen analyzer devices 34 (see FIG. 1). The data acquisition and recording system 50 preferably comprises a user interface software 58 (see FIG. 2) to monitor and control the OAS 10 (see FIG. 2).

As shown in FIG. 7, the oxygen analysis method 200 further comprises step 204 of continuously drawing fuel tank gas samples 70a (see FIG. 2) from aircraft fuel tanks 22 (see FIG. 2). As shown in FIG. 7, the oxygen analysis method 200 further comprises step 206 of introducing a fuel tank gas sample 70a (see FIG. 2) of interest to a tunable laser diode oxygen sensor 64a (see FIG. 2) of the OAS 10 (see FIG. 2). As shown in FIG. 7, the oxygen analysis method 200 further comprises step 208 of measuring with the tunable laser diode oxygen sensor 64a (see FIG. 2) an oxygen concentration 66 (see FIG. 2) of the fuel tank gas sample 70a (see FIG. 2) of interest.

As shown in FIG. 7, the oxygen analysis method 200 further comprises step 210 of drawing an NGS ASM exit gas sample 70b (see FIG. 2) from an NGS ASM exit 26 (see FIG. 1). As shown in FIG. 7, the oxygen analysis method 200 further comprises step 212 of introducing an NGS ASM exit gas sample 70b (see FIG. 2) of interest to the tunable laser diode oxygen sensor 64a (see FIG. 2). As shown in FIG. 7, the oxygen analysis method 200 further comprises step 214 of measuring with the tunable laser diode oxygen sensor 64a (see FIG. 2) an oxygen concentration 66 (see FIG. 2) of the NGS ASM exit sample 70b (see FIG. 2) of interest.

As shown in FIG. 7, the oxygen analysis method 200 further comprises step 216 of outputting to a data acquisition and recording system 50 (see FIGS. 1-3) output results 94 (see FIG. 2) of oxygen concentration data 68 (see FIG. 2) measured by the tunable laser diode oxygen sensor 64a (see FIG. 2). As shown in FIG. 7, the oxygen analysis method 200 further comprises step 218 of monitoring and recording oxygen concentration 66 (see FIG. 2) in the aircraft fuel tanks 22 (see FIGS. 1-3) in real time.

The oxygen analysis method 200 may further comprise the step of performing automated calibration of the OAS 10 (see FIG. 2) using one or more calibration gas concentration values 110 (see FIG. 2) obtained from the supply of calibration gases 112 (see FIG. 2) to calibrate the OAS 10 (see FIG. 2) in real time. The oxygen analysis method 200 may further comprise the step of introducing into an enclosure 62 (see FIG. 3) of each oxygen analyzer device 34 (see FIG. 3) a purge gas 124a (see FIG. 3) comprising an oxygen gas having a 3% oxygen concentration to control the plurality of valves 120 (see FIG. 2) and to provide a purge capability in real time to clear any blocked sample flow channels 80 of the transport tubing assembly 40 (see FIG. 2).

The oxygen analysis method 200 may further comprise the step of using a sensor monitoring system 100 (see FIG. 2) to monitor the tunable laser diode oxygen sensor 64a (see FIG. 2) at a sample rate 106 (see FIG. 2) equal to or greater than about one (1) sample per thirty (30) seconds per sample flow channel 80 (see FIG. 2). The oxygen analysis method 200 may further comprise the step of introducing into an enclosure 62 (see FIG. 3) of each oxygen analyzer device 34 (see FIG. 3) an enclosure inerting gas 102 (see FIG. 3) comprising an oxygen gas having a 3% oxygen concentration to maintain the enclosure at a 3% oxygen concentration throughout an aircraft flight duration.

As shown in FIG. 7, the oxygen analysis method 200 further comprises step 220 of returning the fuel tank gas sample 70a (see FIG. 2) back to the aircraft fuel tank 22 (see FIGS. 1-3) it came from and venting the NGS ASM exit gas sample 70b (see FIG. 2) out of the aircraft 12 (see FIGS. 1, 2).

Figure 8:
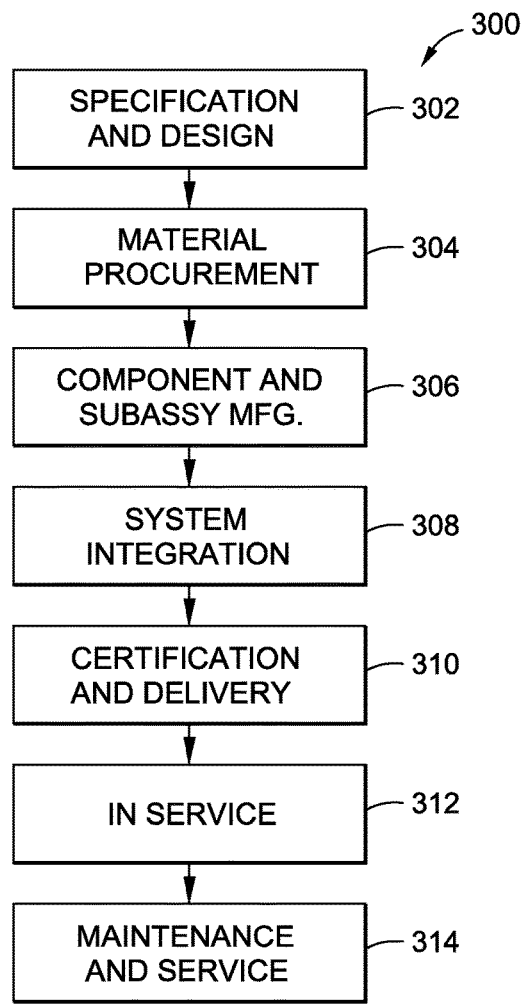
FIG. 8 is an illustration of a flow diagram of an aircraft production and service method; and, FIG. 9 is an illustration of a block diagram of an aircraft.
Figure 9:
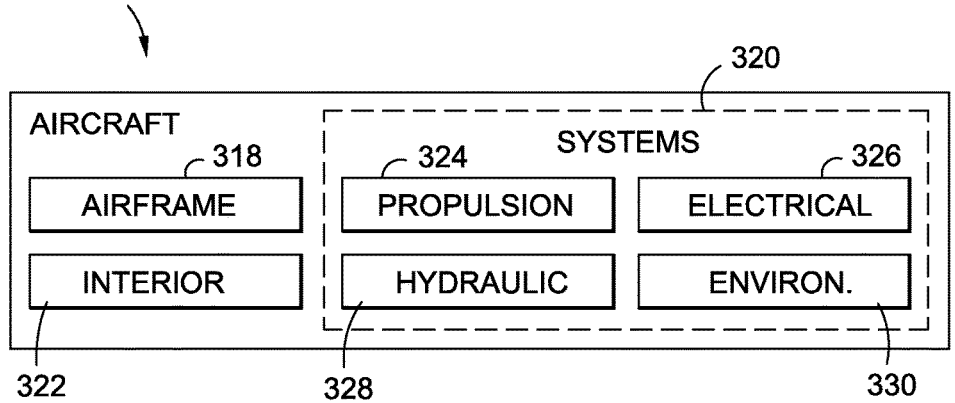

FIG. 8 is an illustration of a flow diagram of an aircraft production and service method 300. FIG. 9 is an illustration of a block diagram of an aircraft 316. Referring to FIGS. 8-9, embodiments of the disclosure may be described in the context of the aircraft production and service method 300, as shown in FIG. 8, and the aircraft 316, as shown in FIG. 9. During pre-production, exemplary aircraft production and service method 300 may include specification and design 302 of the aircraft 316 and material procurement 304. During production, component and subassembly manufacturing 306 and system integration 308 of the aircraft 316 takes place. Thereafter, the aircraft 316 may go through certification and delivery 310 in order to be placed in service 312. While in service 312 by a customer, the aircraft 316 may be scheduled for routine maintenance and service 314 which may also include modification, reconfiguration, refurbishment, and other suitable services.

Each of the processes of the aircraft production and service method 300 may be performed or carried out by a system integrator, a third party and/or an operator (e.g., a customer). For the purposes of this description, a system integrator may include without limitation any number of aircraft manufacturers and major-system subcontractors; a third party may include without limitation any number of vendors, subcontractors and suppliers; and, an operator may be an airline, leasing company, military entity, service organization and other suitable operators.

As shown in FIG. 9, the aircraft 316 produced by exemplary aircraft production and service method 300 may include an airframe 318 with a plurality of high-level systems 320 and an interior 322. Examples of the plurality of high-level systems 320 may include one or more of a propulsion system 324, an electrical system 326, a hydraulic system 328, and an environmental system 330. Any number of other systems may also be included. Although an aerospace example is shown, the principles of the invention may be applied to other industries, such as the automotive industry.

Methods and systems embodied herein may be employed during any one or more of the stages of the production and service method 300. For example, components or subassemblies corresponding to component and subassembly manufacturing 306 may be fabricated or manufactured in a manner similar to components or subassemblies produced while the aircraft 316 is in service 312. Also, one or more apparatus embodiments, method embodiments, or a combination thereof, may be utilized during component and subassembly manufacturing 306 and system integration 308, for example, by substantially expediting assembly of or reducing the cost of the aircraft 316. Similarly, one or more of apparatus embodiments, method embodiments, or a combination thereof, may be utilized while the aircraft 316 is in service 312, for example and without limitation, to routine maintenance and service 314.

Disclosed embodiments of the oxygen analysis system (OAS) 10 (see FIGS. 1-3) and oxygen analysis method 200 (see FIG. 7) of the disclosure provide a system and method that are automated and are designed to measure, monitor and record oxygen concentrations 68 (see FIG. 2) in aircraft fuel tanks 22 (see FIGS. 1-3) and at a nitrogen generation system (NGS) air separation module (ASM) exit 26 (see FIG. 1). The oxygen analysis system (OAS) 10 (see FIGS. 1-3) and oxygen analysis method 200 (see FIG. 7) can measure the oxygen concentration 66 (see FIG. 2) for multiple sample locations 72 (see FIG. 2) in real time and continuously over an aircraft flight duration and can output oxygen concentration data 68 (see FIG. 2) to the data acquisition and recording system 50 (see FIGS. 1-3) for post-flight analysis and can do it in a manner that provides much higher data quality than known systems. For example, the oxygen analysis system (OAS) 10 (see FIGS. 1-3) and oxygen analysis method 200 (see FIG. 7) can measure gas samples 70 (see FIG. 2) from up to 21 sample locations 72 (see FIG. 2) in the aircraft fuel tanks 22 (see FIG. 2), and from one sample location 72 (see FIG. 2) at the NGS ASM exit gas sampling port 28 (see FIGS. 1, 2). Preferably, disclosed embodiments of the oxygen analysis system (OAS) 10 (see FIGS. 1-3) and oxygen analysis method 200 (see FIG. 7) of the disclosure may be used in a flight test aircraft to certify a Nitrogen Generation System (NGS).

In addition, disclosed embodiments of the oxygen analysis system (OAS) 10 (see FIGS. 1-3) and oxygen analysis method 200 (see FIG. 7) provide a faster, more stable system and method of measuring and recording the oxygen concentration data 68 (see FIG. 2) with less drift in measurement readings, and they improve the sample rate 106 (see FIG. 2) for taking gas samples 70 (see FIG. 2) at sample locations 72 (see FIG. 2). Moreover, the oxygen analysis system (OAS) 10 (see FIGS. 1-3) has an increased responsiveness and may detect changes in oxygen concentrations 66 (see FIG. 2) more rapidly than known systems, provides an automated, multi-channel (i.e., up to four sample flow channels 80 (see FIG. 2)), a high-rate sampling system and method, an automated in situ calibration and measurement verification feature, an automated purge function, and oxygen concentration data 68 (see FIG. 2) quality output results 94 (see FIG. 2), such as oxygen concentration measurements, to confirm the health of the oxygen sensor 64 (see FIG. 2).

Further, disclosed embodiments of the oxygen analysis system (OAS) 10 (see FIGS. 1-3) requires decreased maintenance by a user or operator of the OAS 10 to ensure the OAS 10 provides reasonable output results 94 (see FIG. 2), and the oxygen analysis system (OAS) 10 (see FIGS. 1-3) and oxygen analysis method 200 (see FIG. 7) may be critical for meeting certification requirements of nitrogen generation system (NGS) systems now required on commercial aircraft. The disclosed oxygen analysis system (OAS) 10 (see FIGS. 1-3) and oxygen analysis method 200 (see FIG. 7) use an automated user interface software 58 (see FIG. 2) for lab tests and flight tests that provide operator selectable scan configurations, real-time calibration and observation, and pause capabilities. In addition, the disclosed oxygen analysis system (OAS) 10 (see FIGS. 1-3) and oxygen analysis method 200 (see FIG. 7) provide output results 94 (see FIG. 2) for recording via ARINC 429 (a communications protocol that transmits data) to an existing flight test data acquisition and recording system, use a laser diode spectroscopy sensor that is tuned to oxygen, use an automated 2-point automated calibration system 108 (see FIG. 2) with precision calibration gases, and provide an automatic and manual purge (back-flow) capability to clear blocked channels using a purge (and valve control) gas 124*a* (see FIG. 3) having an oxygen concentration of 3%.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. An oxygen analysis system (OAS) for measuring, monitoring and recording oxygen concentration in aircraft fuel tanks, the oxygen analysis system comprising:
    a rack support structure installed in an interior aircraft cabin of an aircraft, the rack support structure having an oxygen analyzer device portion on one side and having a plumbing portion on an opposite side;
    a plurality of oxygen analyzer devices and at least one nitrogen-enriched air (NEA) analyzer device stacked vertically within the oxygen analyzer device portion of the rack support structure, each oxygen analyzer device comprising an oxygen sensor to measure oxygen concentration in gas samples continuously drawn from sample locations in aircraft fuel tanks and at an aircraft nitrogen generation system (NGS) air separation module (ASM) exit;
    a plurality of plumbing system control displays stacked vertically and mounted to the plumbing portion of the rack support structure opposite the oxygen analyzer device portion, the plurality of plumbing system control displays comprising a verification gas control, an NGS ASM exit gas sampling port control, fuel tank gas sample line controls, a return flow control, a purge flow adjustment valve control, an inlet test port control, and a return test port control;
    a supply of calibration gases housed within the rack support structure behind the plumbing portion, the supply of calibration gases calibrating the oxygen analysis system (OAS) in real time, and consisting of an oxygen gas having a 5% oxygen concentration and an oxygen gas having a 21% oxygen concentration;
    a verification gas consisting of an oxygen gas having a 12% oxygen concentration, the verification gas controlled with the verification gas control coupled to the rack support structure;
    a plurality of valves, including a selection valve to select one of the calibration gases, or the verification gas, as a gas sample to be analyzed by the oxygen sensor, a supply of purge and operating gases, and a power distribution assembly, all coupled to the rack support structure;
    a transport tubing assembly coupled between the rack support structure and the aircraft fuel tanks and the aircraft NGS ASM exit, the transport tubing assembly configured to transport the gas samples to and from the plurality of oxygen analyzer devices in the rack support structure;
    a transport tubing inspection point for the transport tubing assembly, the transport tubing inspection point located in an interior cargo bay of the aircraft, the interior cargo bay and the interior aircraft cabin being located in separate locations in the aircraft and separate from the aircraft fuel tanks, and the interior cargo bay being positioned below the interior aircraft cabin;
    a plurality of fuel tank gas sampling ports located in the aircraft fuel tanks;
    an NGS ASM exit gas sampling port located at the aircraft NGS ASM exit;
    a drain manifold assembly coupled along the transport tubing assembly between the rack support structure and the plurality of fuel tank gas sampling ports and configured to capture and drain liquids that enter into the transport tubing assembly; and,
    a data acquisition and recording system coupled to the plurality of oxygen analyzer devices, for collecting and processing oxygen concentration data measured by the oxygen sensor of each oxygen analyzer device, the data acquisition and recording system comprising a user interface software to monitor and control the oxygen analysis system.

2. The oxygen analysis system of claim 1, further comprising a sensor monitoring system to monitor the oxygen sensor of each oxygen analyzer device at a sample rate equal to or greater than about one (1) sample per thirty (30) seconds per sample flow channel.

3. The oxygen analysis system of claim 1, further comprising an automated calibration system using one or more calibration gas concentration values obtained from the supply of calibration gases to calibrate the oxygen analysis system in real time.

4. The oxygen analysis system of claim 1, wherein the oxygen analysis system (OAS) is used in a flight test aircraft to certify a Nitrogen Generation System (NGS).

5. The oxygen analysis system of claim 1, wherein the plurality of valves further comprises a plurality of float valves comprising fuel tank sample float valves and fuel tank return float valves, the plurality of float valves preventing ingestion of liquid fuel at the sample locations.

6. The oxygen analysis system of claim 1, wherein the supply of purge and operating gases comprises a purge gas comprising an oxygen gas having a 3% oxygen concentration to control the plurality of valves and to provide a purge capability in real time to clear blocked sample flow channels of the transport tubing assembly.

7. The oxygen analysis system of claim 1, further comprising an enclosure inerting gas comprising an oxygen gas having a 3% oxygen concentration to maintain an enclosure of each oxygen analyzer device at a 3% oxygen concentration throughout an aircraft flight duration.

8. The oxygen analysis system of claim 1 wherein the oxygen sensor is a tunable laser diode oxygen sensor.

9. The oxygen analysis system of claim 1 wherein the plurality of fuel tank gas sampling ports comprise up to twenty-one (21) sample locations in the aircraft fuel tanks.

10. The oxygen analysis system of claim 1 wherein the gas samples drawn from sample locations within the aircraft fuel tanks are drawn from an ullage of each aircraft fuel tank.

11. The oxygen analysis system of claim 1 wherein the oxygen analysis system (OAS) is a flight test data acquisition and monitoring system designed for real-time measurement and monitoring of oxygen concentration.

12. An aircraft comprising:
    at least one wing, each wing having one or more aircraft fuel tanks;

a fuselage defining an interior aircraft cabin and an interior cargo bay; and, an oxygen analysis system (OAS) comprising:

a rack support structure installed in the interior aircraft cabin, the rack support structure having an oxygen analyzer device portion on one side and having a plumbing portion on an opposite side;

a plurality of oxygen analyzer devices and at least one nitrogen-enriched air (NEA) analyzer device stacked vertically within the rack support structure, each oxygen analyzer device comprising a tunable laser diode oxygen sensor to measure oxygen concentration in gas samples continuously drawn from sample locations in the aircraft fuel tanks and at an aircraft nitrogen generation system (NGS) air separation module (ASM) exit;

a plurality of plumbing system control displays stacked vertically and mounted to the plumbing portion of the rack support structure opposite the oxygen analyzer device portion, the plurality of plumbing system control displays comprising a verification gas control, an NGS ASM exit gas sampling port control, fuel tank gas sample line controls, a return flow control, a purge flow adjustment valve control, an inlet test port control, and a return test port control;

a supply of calibration gases housed within the rack support structure behind the plumbing portion, the supply of calibration gases calibrating the oxygen analysis system (OAS) in real time, and consisting of an oxygen gas having a 5% oxygen concentration and an oxygen gas having a 21% oxygen concentration;

a verification gas consisting of an oxygen gas having a 12% oxygen concentration, the verification gas controlled with a the verification gas control coupled to the rack support structure;

a plurality of valves, including a selection valve to select one of the calibration gases, or the verification gas, as a gas sample to be analyzed by the oxygen sensor, a supply of purge and operating gases, and a power distribution assembly, all coupled to the rack support structure;

a transport tubing assembly coupled between the rack support structure and the aircraft fuel tanks and the aircraft NGS ASM exit, the transport tubing assembly configured to transport the gas samples to and from the plurality of oxygen analyzer devices in the rack support structure;

a transport tubing inspection point for the transport tubing assembly, the transport tubing inspection point located in the interior cargo bay of the aircraft, the interior cargo bay and the interior aircraft cabin being located in separate locations in the aircraft and separate from the aircraft fuel tanks, and the interior cargo bay being positioned below the interior aircraft cabin;

a plurality of fuel tank gas sampling ports located in the aircraft fuel tanks;

an NGS ASM exit gas sampling port located at the aircraft NGS ASM exit;

a drain manifold assembly coupled along the transport tubing assembly between the rack support structure and the plurality of fuel tank gas sampling ports and configured to capture and drain liquids that enter into the transport tubing assembly; and, a data acquisition and recording system coupled to the plurality of oxygen analyzer devices, for collecting and processing oxygen concentration data measured by the tunable laser diode oxygen sensor of each oxygen analyzer device, the data acquisition and recording system comprising a user interface software to monitor and control the oxygen analysis system, wherein the oxygen analysis system measures, monitors and records oxygen concentration in the aircraft fuel tanks in real time.

13. The aircraft of claim 12 wherein the oxygen analysis system further comprises a sensor monitoring system to monitor the oxygen sensor of each oxygen analyzer device at a sample rate equal to or greater than about one (1) sample per thirty (30) seconds per sample flow channel.

14. The aircraft of claim 12 wherein the oxygen analysis system further comprises an automated calibration system using one or more calibration gas concentration values obtained from the supply of calibration gases to calibrate the oxygen analysis system in real time.

15. The aircraft of claim 12 wherein the oxygen analysis system further comprises an enclosure inerting gas and a purge gas both comprising an oxygen gas having a 3% oxygen concentration.

16. An oxygen analysis method for measuring, monitoring and recording oxygen concentration in aircraft fuel tanks, the method comprising the steps of:

installing an oxygen analysis system (OAS) in an aircraft, the oxygen analysis system (OAS) comprising:

a rack support structure installed in an interior aircraft cabin of an aircraft, the rack support structure having an oxygen analyzer device portion on one side and having a plumbing portion on an opposite side;

a plurality of oxygen analyzer devices and at least one nitrogen-enriched air (NEA) analyzer device stacked vertically within the oxygen analyzer device portion of the rack support structure, each oxygen analyzer device comprising a tunable laser diode oxygen sensor;

a plurality of plumbing system control displays stacked vertically and mounted to the plumbing portion of the rack support structure opposite the oxygen analyzer device portion, the plurality of plumbing system control displays comprising a verification gas control, a nitrogen generation system (NGS) air separation module (ASM) exit gas sampling port control, fuel tank gas sample line controls, a return flow control, a purge flow adjustment valve control, an inlet test port control, and a return test port control;

a supply of calibration gases housed within the rack support structure behind the plumbing portion, the supply of calibration gases calibrating the oxygen analysis system (OAS) in real time, and consisting of an oxygen gas having a 5% oxygen concentration and an oxygen gas having a 21% oxygen concentration;

a verification gas consisting of an oxygen gas having a 12% oxygen concentration, the verification gas controlled with the verification gas control coupled to the rack support structure;

a plurality of valves, including a selection valve to select one of the calibration gases, or the verification gas, as a gas sample to be analyzed by the oxygen sensor, a supply of purge and operating gases, and a power distribution assembly, all coupled to the rack support structure;

a plurality of fuel tank gas sampling ports located in the aircraft fuel tanks;

a nitrogen generation system (NGS) air separation module (ASM) exit gas sampling port located at an aircraft nitrogen generation system (NGS) air separation module (ASM) exit;

a transport tubing assembly coupled between the rack support structure and the fuel tank gas sampling ports and the NGS ASM exit gas sampling port;

a transport tubing inspection point for the transport tubing assembly, the transport tubing inspection point located in an interior cargo bay of the aircraft, the interior cargo bay and the interior aircraft cabin being located in separate locations in the aircraft and separate from the aircraft fuel tanks, and the interior cargo bay being positioned below the interior aircraft cabin;

a drain manifold assembly coupled to the transport tubing assembly; and the data acquisition and recording system coupled to the plurality of oxygen analyzer devices, the data acquisition and recording system comprising a user interface software to monitor and control the oxygen analysis system;

continuously drawing fuel tank gas samples from aircraft fuel tanks;

introducing a fuel tank gas sample of interest to the tunable laser diode oxygen sensor of the OAS;

measuring with the tunable laser diode oxygen sensor an oxygen concentration of the fuel tank gas sample of interest;

drawing an NGS ASM exit gas sample of interest from the aircraft NGS ASM exit;

introducing the NGS ASM exit gas sample of interest to the tunable laser diode oxygen sensor;

measuring with the tunable laser diode oxygen sensor an oxygen concentration of the NGS ASM exit gas sample of interest;

outputting to a data acquisition and recording system output results of oxygen concentration data measured by the tunable laser diode oxygen sensor;

monitoring and recording oxygen concentration in the aircraft fuel tanks in real time; and, returning the fuel tank gas sample of interest back to the aircraft fuel tank it came from and venting the NGS ASM exit gas sample of interest out of the aircraft.

17. The method of claim 16 wherein the step of installing the OAS in the aircraft comprises installing the OAS further comprising the plurality of valves further comprising a plurality of float valves comprising fuel tank sample float valves and fuel tank return float valves, the plurality of float valves preventing ingestion of liquid fuel at the sample locations.

18. The method of claim 16 further comprising the step of performing automated calibration of the oxygen analysis system using one or more calibration gas concentration values obtained from the supply of calibration gases to calibrate the oxygen analysis system in real time.

19. The method of claim 16 further comprising the step of introducing into an enclosure of each oxygen analyzer device a purge gas comprising an oxygen gas having a 3% oxygen concentration to control the plurality of valves and to provide a purge capability in real time to clear any blocked sample flow channels of the transport tubing assembly.

20. The method of claim 16 further comprising the step of introducing into an enclosure of each oxygen analyzer device an enclosure inerting gas comprising an oxygen gas having a 3% oxygen concentration to maintain the enclosure at a 3% oxygen concentration throughout an aircraft flight duration.

21. The method of claim 16 further comprising the step of using a sensor monitoring system to monitor the tunable laser diode oxygen sensor at a sample rate equal to or greater than about one (1) sample per thirty (30) seconds per sample flow channel.

* * * * *